US006210906B1

United States Patent
Kundu et al.

(10) Patent No.: US 6,210,906 B1
(45) Date of Patent: Apr. 3, 2001

(54) SPECIFIC ANTIBODIES TO KRINGLE 5 OF APO(A) AND METHODS OF USE THEREFOR

(75) Inventors: Samar K. Kundu, Libertyville; Robert N. Ziemann, Wildwood, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/234,553

(22) Filed: Jan. 20, 1999

Related U.S. Application Data

(60) Provisional application No. 60/072,924, filed on Jan. 20, 1998.

(51) Int. Cl.$^7$ ............................. G01N 33/53; G01N 33/48
(52) U.S. Cl. ................................ 435/7.1; 435/11; 435/4; 436/2; 436/63; 436/71; 436/518; 436/523; 436/526; 436/527; 436/530; 436/534; 436/535; 436/547; 436/548; 436/808
(58) Field of Search ...................... 436/2, 63, 71, 436/518, 523, 526, 527, 530, 534, 535, 547, 548, 808; 435/7.1, 11, 4

(56) References Cited

U.S. PATENT DOCUMENTS

| | | |
|---|---|---|
| 4,945,040 | 7/1990 | Fless et al. . |
| 5,187,098 | 2/1993 | Malke et al. . |
| 5,229,073 | 7/1993 | Luo et al. . |
| 5,272,166 | * 12/1993 | Breslow et al. ................... 514/390 |
| 5,278,189 | * 1/1994 | Rath et al. ....................... 514/561 |

(List continued on next page.)

FOREIGN PATENT DOCUMENTS

| | | |
|---|---|---|
| 0 621 284 A1 | 10/1994 | (EP) . |
| 0 764 657 A1 | 3/1997 | (EP) . |
| 93/18067 | 9/1993 | (WO) . |
| 94/00483 | 1/1994 | (WO) . |
| WO 96/00903 | 1/1996 | (WO) . |
| 96/19500 | 6/1996 | (WO) . |
| 97/17371 | 5/1997 | (WO) . |

OTHER PUBLICATIONS

McLean et al. "cDNA sequence of human apolipoprotein (a) is homologous to plasminogen". Nature vol. 330: Nov. 12, 1987, pp.: 132–137.*

Albers et al. (1990) Clin Chem 36: 2019–2026, "The Unique Lipoprotein (a): Properties and Immunochemical Measurement".

Albers and Marcovina (1994) Curr Opin in Lipidology 5: 417–421, "Lipoprotein (a) quantification: comparison of methods and strategies for standardization".

Chenivesse, et al. (1996) Protein Expression and Purification 8:145–150, "Expression of a Recombinant Kringle V of Human Apolipoprotein(a): Antibody Characterization and Species Specificity".

(List continued on next page.)

*Primary Examiner*—Long V. Le
*Assistant Examiner*—Pensee T. Do
(74) *Attorney, Agent, or Firm*—Dianne Casuto

(57) ABSTRACT

The present invention provides monoclonal antibodies specific for kringle 5 of apo(a) and hybridomas secreting such antibodies. The invention also relates to assay methods for directly measuring concentrations of lipoprotein(a) [Lp(a)] in a plasma sample. In one embodiment, the method involves the specific capture of Lp(a) from a plasma sample with a monoclonal antibody developed against kringle 5 of apo(a), which is non-cross-reactive with plasminogen and kringle 4 of apo(a). The quantity of the Lp(a) present in the sample is then measured by detecting the amount of Lp(a)-anti-kringle 5 complex that has formed in the reaction. Alternatively, the Lp(a) may be captured non-specifically and then detected with the monoclonal antibody specific for kringle 5 of apo(a). The invention also provides competitive assays using the above-mentioned kringle 5 specific monoclonal antibodies.

26 Claims, 18 Drawing Sheets

U.S. PATENT DOCUMENTS

| | | |
|---|---|---|
| 5,320,968 | 6/1994 | Seman . |
| 5,490,981 | 2/1996 | Chiknas . |
| 5,597,908 | 1/1997 | Taddei-Peters et al. . |
| 5,712,157 * | 1/1998 | Marcovina et al. ............... 435/337 |
| 5,721,138 * | 2/1998 | Lawn ................................. 435/325 |
| 5,786,156 * | 7/1998 | Taddei-Peters et al. ........... 435/7.9 |
| 5,874,544 * | 2/1999 | Taddei-Peters et al. ......... 530/387.9 |
| 5,981,484 * | 11/1999 | Davidson ............................. 514/2 |

OTHER PUBLICATIONS

Church, et al. (1994) Hybridoma, vol. 13, No. 5, pp. 423–429, A Kringle–Specific Monoclonal Antibody.

Dieplinger, et al. (1995), Journal of Lipid Research, vol. 36, pp. 813–821, "Kringle 4 of human apolipoprotein [a] shares a linear antigenic site with human catalase".

Eaton, et al. (1987) Proc. Natl. Acad. Sci USA 84, Biochemistry, vol. 84, pp. 3224–3228, "Partial amino acid sequence of apolipoprotein (a) shows that it is homologous to plasminogen".

Edelstein, et al. (1996) Journal of Lipid Research, vol. 37, pp. 1786–1801 Functional and metabolic differences between elastase–generated fragments of human lipoprotein [a]and apolipoprotein [a].

Fless, et al. (1989) Journal of Lipid Research 30:651–662, "Enzyme–linked immunoassay for Lp[a]".

Gaubatz, et al. (1986), Methods in Enzymology, vol. 129 pp. 167–187 "Quantitation, Isolation, and Characterization of Human Lipoprotein (a)".

Keesler, et al. (1996) Journal of Biol Chem 271: 32096–32104, The Binding Activity of the Macrophage Lipoprotein (a) / Apolipoprotein (a) Receptor is Induced by Cholesterol via a Post–translational Mechanism and Recognizes Distinct Kringle Domains on Apolipoprotein (a) *.

Klezovitch, et al. (1995) Current Opin in Lipidology 6:223–228, "Heterogeneity of lipoprotein (a) growing complexities".

Labeur and Rosseneu (1992) Current Opin in Lipidology 3: 372–376, "Methods for the measurement of lipoprotein (a) in the clinical laboratory".

Lackner, et al., Human Molec. Genetics (1993) 2: 933–940, "Molecular definition of the extreme size polymorphism in apolipoprotein (a)".

Lafferty et al. (1991) Journal of Lipid Research 32: 277–292, "Immunochemistry of human Lp[a]: characterization of monoclonal antibodies that cross–react strongly with plasminogen".

Li, et al. (1992) Protein Express. And Purif. 3:212–222, "Expression and Purification of Kringle 4–Type 2 of Human Apolipoprotein (a) in *Escherichia coli*".

Marcovina, et al. (1995) Clin Chem 41/2: 246–255, "Effect of the Number of Apolipoprotein(a) Kringle 4 Domains on Immunochemical Measurements of Lipoprotein(a)".

Marcovina, et al. (1995) Current Opinion in Lipidology, 6:136–145, "Structure and metabolism of lipoprotein (a)".

McLean, et al. (1987) Nature 330:132–137, "cDNA sequence of human apolipoprotein (a) is homologous to plasminogen".

Morrisett, et al. (1987) in Plasma Lipoproteins, Elsevier Science B.V., Chapter 4 pp. 129–152. "Lipoprotein (a): structure, metabolism and epidemiology".

Rainwater and Manis, 1988 Atherosclerosis 73: 23–31, "Immunochemical characterization and quantitation of lipoprotein (a) in baboons".

van der Hoek, et al. Human Molecular Genetics (1993) 2: 361–366, "The apolipoprotein(a) kringle IV repeats which differ from the major repeat kringle are present in variably–sized isoforms".

Wong, et al., A Monoclonal–Antibody–Based Enzyme–Linked Immunosorbent Assay of Lipoprotein (a), Clinical Chemistry, vol. 36, No. 2, 1990, pp. 192–197.

* cited by examiner

PSEQDCMFGNGKGYRGKKATTVTGTPCQEWAAQEPHRHSTFIPGTNKWAGLEKN
YCRNPDGDINGPWCYTMNPRKLFDYCDIPLCASSSFD

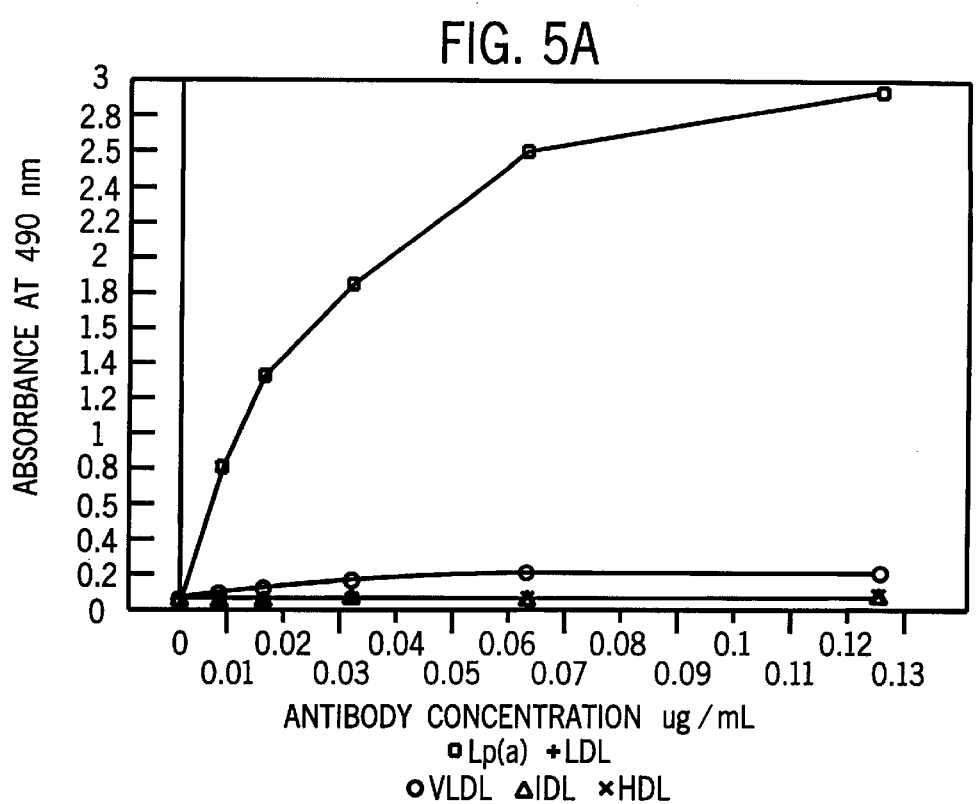
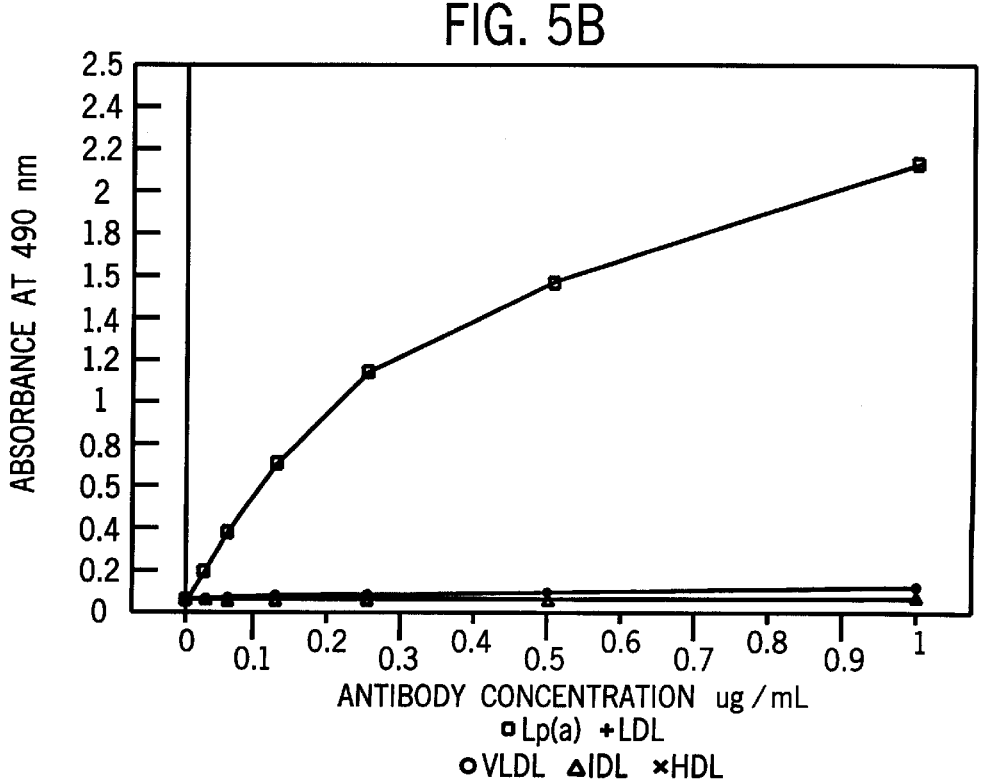

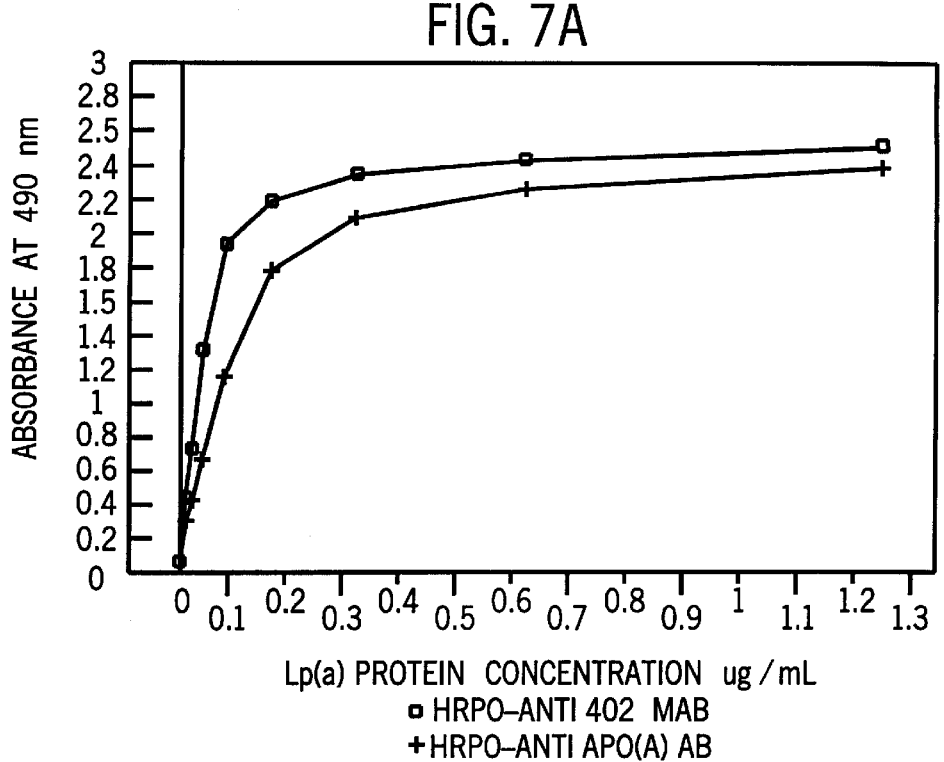
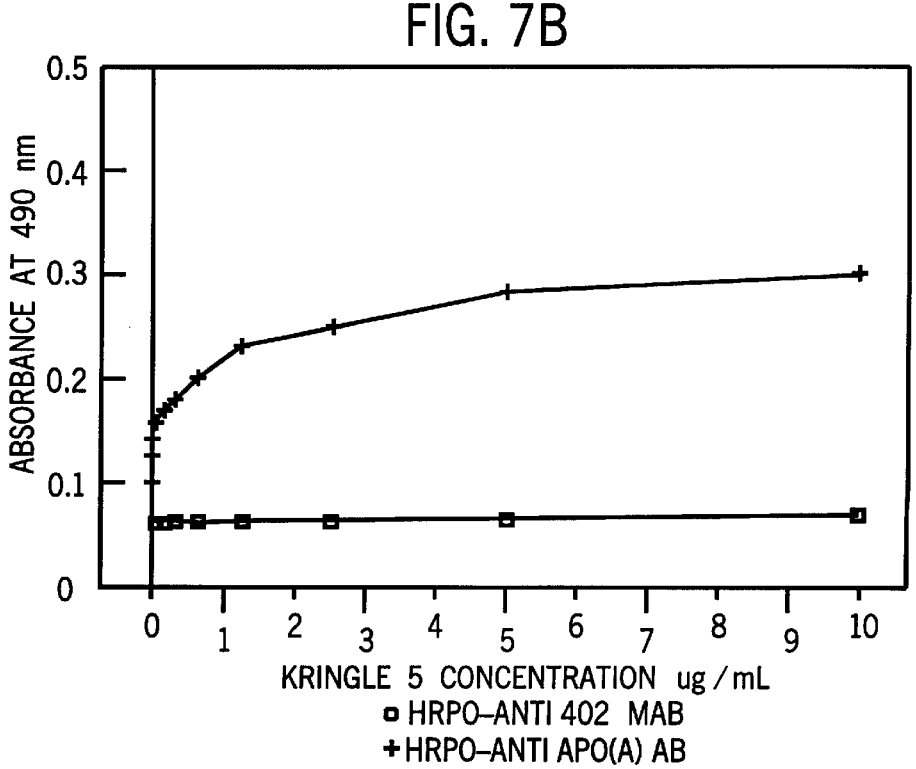

SEQUENCE LISTING

<160> NUMBER OF SEQ ID NOS: 1

<210> SEQ ID NO 1
<211> LENGTH: 91
<212> TYPE: PRT
<213> ORGANISM: Homo sapiens

<400> SEQUENCE: 1

Pro Ser Glu Gln Asp Cys Met Phe Gly Asn Gly Lys Gly Tyr Arg Gly
 1               5                  10                  15

Lys Lys Ala Thr Thr Val Thr Gly Thr Pro Cys Gln Glu Trp Ala Ala
             20                  25                  30

Gln Glu Pro His Arg His Ser Thr Phe Ile Pro Gly Thr Asn Lys Trp
         35                  40                  45

Ala Gly Leu Glu Lys Asn Tyr Cys Arg Asn Pro Asp Gly Asp Ile Asn
     50                  55                  60

-continued

```
Gly Pro Trp Cys Tyr Thr Met Asn Pro Arg Lys Leu Phe Asp Tyr Cys
65                  70                  75                  80

Asp Ile Pro Leu Cys Ala Ser Ser Phe Asp
                85              90
```

SPECIFIC ANTIBODIES TO KRINGLE 5 OF APO(A) AND METHODS OF USE THEREFOR

RELATED APPLICATIONS

This application claims priority under 35 U.S.C. §119(e) to provisional application U.S. Ser. No. 60/072,924, filed Jan. 20, 1998, the disclosure of which is incorporated by reference herein.

FIELD OF THE INVENTION

The present invention relates generally to antibodies which specifically bind to kringle 5 of apo(a), to hybridoma cell lines which secrete those antibodies, to methods of using the antibodies and to kits for measuring lipoprotein (a) from plasma.

BACKGROUND OF THE INVENTION

Lipoprotein(a) [Lp(a)] was described as a genetic variant of low density lipoprotein (LDL) in 1963 (K. Berg (1963) Acta Pathol Microbiol Scand 59: 369–381). Later it was discovered that although Lp(a) resembles LDL in having similar lipid composition and a common apolipoprotein B-100 (apo B), Lp(a) contains an additional glycoprotein, named apolipoprotein(a) [apo(a)]. Each Lp(a) molecule contains one molecule of apo(a) per one molecule of apo B covalently linked by a sulfide bond that can be easily reduced to LDL and apo(a) (Gaubatz et al. (1983) J. Biol Chem 258: 4582–4589; Fless et al. (1984) J. Biol Chem 259: 11470–11478; Fless et al. (1986) J Biol Chem 261: 8712–8718, Fless et al (1994) Biochemistry 33: 13492–13501; Marcovina and Morrisett (1995) Curr Opin in Lipidology 6: 136–145; Albers et al. (1996) J Lipid Res 37: 192–196).

Lipoprotein(a) particles exhibit considerable inter- and intra-individual heterogeneity, with some individuals exhibiting two or more distinct Lp(a) particles differing in hydrated density (Fless et al. (1984) J Biol Chem 259: 11470–11478). Also, the Lp(a) particle varies widely in size, with the size heterogeneity related primarily to the size of the apo(a) isoforns, ranging from 280 to 838 KDa; to date, 34 different isoforms have been identified (Marcovina et al. (1993) Biochem Biophys Res Commun 191: 1192–1196). The number of apo(a) isoforms that can be distinguished varies from six to at least twelve isoforms. The smaller isoforms are generally present at less frequency and are associated with the higher Lp(a) concentrations, whereas the larger isoforms have a higher frequency and are associated with lower Lp(a) concentrations. There appears to be an inverse relationship between the apparent molecular mass of the apo(a) isoforms and the concentrations of Lp(a) in plasma (G. Utermann (1989) Science 246: 904–910; Morrisett et al. (1990) in Lipoprotein(a), Academic Press, pp. 53–74; Sandholzer et al. (1992) Arteriosclerosis and Thrombosis 12: 1212–1226).

The structural gene for apo(a) is located on chromosome 6 near the plasminogen gene (Frank et al. (1988) Hum Genet 79: 352–356). Sequencing of apo(a) at both the protein and cDNA level has revealed a high degree of homology to plasminogen (Eaton et al. (1987) Proc Natl Acad Sci 84: 3224–3228; McLean et al. (1987) Nature (London) 330: 132–137). Apo(a) contains two types of plasminogen-like domains: a single kringle 5 domain, with 82% amino acid sequence homology and 91% nucleotide sequence homology with plasminogen, and multiple repeats of a kringle 4 domain, with 61–75% amino acid homology and 75–85% nucleotide sequence homology with the kringle 4 domain of plasminogen. Homology to plasminogen is also revealed by immunochemical studies that show cross-reactivity of apo (a) and plasminogen (Karadi et al. (1988) Biochim Biophys Acta 960: 91–97); Lafferty et al. (1991 ) J Lipid Res 32: 277–292).

Numerous studies have indicated that elevated levels of Lp(a) in plasma are associated with premature coronary heart disease (CHD) (Scanu and Fless (1990) J Clin Invest 85: 1709–1715; Sandholzer et al. (1992) Arteriosclerosis and Thrombosis 12: 1214–1226; Seed et al. (1990) New Engl J Med 332: 1494–1499; Genest et al. (1992) J Am Coll Cardiol 19: 792–802; Dahlen et al. (1986) Circulation 74: 758–765). Lp(a) concentrations in human plasma range from 1 mg/dL to more than 100 mg/dL. When the plasma Lp(a) level is above 30 mg/dL, the relative risk of CHD is raised about two-fold. When LDL and Lp(a) are both elevated, the relative risk is increased to about five-fold (Armstrong et al. (1986) Atherosclerosis 62: 249–257). Recent studies have suggested that increased Lp(a) concentrations may inhibit fibrinolysis by reducing the generation of plasmin by competing for plasminogen cell-surface receptors, or inhibiting activation of plasminogen, or competing for binding sites on fibrin (Hajjar et al. (1989) Nature (London) 339: 303–305; Miles et al. (1989) Nature (London) 339: 301–303; Gonzalez-Gronow et al. (1989) Biochemistry 28: 2374–2377; Edelberg et al. (1989) Biochemistry 28: 2370–2374; Loscalzo et al. (1990) Anteriosclerosis 10: 240–245; Harpel et al. (1989) Proc Natl Acad Sci USA 86: 3847–3851; Angles-Cano (1994) Chem Phys Lipids 67/68: 353–362; 369–380; Liu et al. (1994) Biochemistry 33: 2554–2560; Hajjar and Nachman (1996) Annu Rev Med 47: 423–442).

More recently, it has been shown that the binding activity of the macrophage Lp(a)/apo(a) receptor can be blocked by a monoclonal antibody directed against a specific kringle 4 domain (subtypes 6–7) (Keesler et al (1996) J Biol Chem 27: 32096–32104). This suggests a possible role of Lp(a) in Lp(a)-induced atherogenesis. While the function of Lp(a) is unknown, a significant correlation has been established between elevated levels of Lp(a) and coronary artery and cardiovascular disease that led many scientists to study the physiological role of Lp(a) in heart disease (R. M. Lawn (1992) Scientific American pp. 54–60; Simon et al. (1993) Curr Opin in Lipidology 8: 814–820; Klezovitz and Scanu (1995) Curr Opin in Lipidology 6: 223–228; Durrington (1995) Bailliere Clin Endocrinol 9: 773–795).

A number of assay methods for quantitating Lp(a) in plasma are known (see Morrisett et al. (1987) in Plasma Lipoproteins, Elsevier Science B. V., Chapter 5, pp. 129–152; Gaubatz et al. (1986) in Methods in Enzymology, Vol. 129, pp. 167–187; Albers et al. (1990) Clin Chem 36: 2019–2026; Labeur and Rosseneu (1992) Curr Opin in Lipidology 3: 372–376; Albers and Marcovina (1994) Curr Opin in Lipidology 5: 417–421). The assays include radioimmunoassays, enzyme-linked immunosorbent assays (ELISAs), radial immunodiffusion, electroimmunoassays, immunoelectrophoresis and turbidimetric assays. Most of the Lp(a) assay methods except the ELISAs are not commonly used due to inherent technical problems (Labeur and Rosseneu (1992) Curr Opin in Lipidology 3: 372–376). ELISAs that are presently known use either monoclonal or affinity-purified polyclonal antibodies. The majority of the monoclonal antibodies recognize the kringle 4 epitope of apo(a), whereas the polyclonal antibodies recognize both kringle 4 and kringle 5 epitopes of apo(a) (Lafferty et al. (1991) J Lipid Res 32: 277–292; Fless et al. (1989) J Lipid Res 30: 651–662; Rainwater and Manis (1988) Atherosclerosis 73: 23–31).

As noted above, apo(a) contains multiple copies of kringle 4 domain. The multiple copies of apo(a) kringle 4 are similar but not identical to each other and can be divided into 10 distinct kringle types (kringle 4 types 1 through 10). One copy each of kringle 4 type 1 and types 3 through 10 is present per apo(a) molecule; kringle 4 type 2, however, is present in a variable number of repeats (from 3 to >40) and are therefore responsible for the size heterogeneity of apo(a) and consequently Lp(a) (Lackner et al. Hum Molec Genet (1993) 2: 933–940; Van der Hoek et al. Hum Molec Genet (1993) 2: 361–366). From the structural sequence of kringle 4 repeats it seems obvious that the immunoreactivity of the antibodies used in the immunoassays to measure Lp(a) concentrations will vary according to the number of epitopes available in a particular Lp(a). Therefore, antibodies against apo(a) should be selected to be specific for that part of the apo(a) molecule that is independent of size polymorphism, i.e. for kringle 4 domains other than type 2 or kringle 5 domain.

Among the numerous papers published to date, only one reports the domain specificity of the monoclonal antibodies used in the immunoassays to measure Lp(a) (Marcovina et al. (1995) Clin. Chem 41: 246–255). Recently, an immunoassay method for the detection of Lp(a) was disclosed using an anti-apo(a) monoclonal antibody that was described as non-reactive with plasminogen and the kringle 4 type 2 repeats of apo(A) (see WO96/19500 published Jun. 27, 1996). Although Albers, Rosseneau, and others have suggested that an optimal antibody should be the one that is directed towards an epitope that is localized in the non-repetitive and non-glycosylated kringle 5 domain (Albers et al. (1990) Clin Chem 36: 2019–2026; Labeur and Rosenau (1992) Curr Opin in Lipidology 3: 372–376; Albers and Marcovina (1994) Curr Opin in Lipidology 5: 417–421), it was not been possible until recently to develop kringle 5 domain specific antibodies because of extensive problems associated with generating domain specific antibodies.

A polyclonal antibody was recently developed by immunizing a sheep with a cloned kringle 5 fusion protein (Chenivesse et al. (1996) Protein Expression and Purification 8: 145–150). This antibody was shown by ELISA and Western blot to react with Lp(a) and the C-terminal domain of apo(a), but not with the kringle 4 repeats at the N-terminal end. In both formats, the proteins were immobilized on solid phases, sometimes under denaturing conditions. No data was provided on whether this polyclonal antibody cross-reacted with plasminogen or any of the other lipoproteins that are abundant in human plasma.

The reactivity of an antibody for its specific antigen can differ considerably depending on the type of assay format it is used in, i.e. how and where in the assay the antibody is utilized. The state of the antigen, e.g. whether it is in solution or attached to a solid phase, how it is attached to a solid phase, whether it is denatured or not, also affects antibody binding; some antibodies recognize conformation-dependent epitopes and therefore require the antigen to be in its native state. Moreover, the specificity and immunoreactivity of polyclonal antibodies can vary from animal to animal and species to species making it difficult to produce a reliable and consistent immunoassay. Therefore, monoclonal antibodies are presently needed which are specific for an epitope(s) that are localized in the kringle 5 domain of apo(a) and do not cross-react with plasminogen or the kringle 4 domain of apo(a). Such monoclonal antibodies may serve as accurate markers for the detection and diagnosis of heart disease.

SUMMARY OF THE INVENTION

One object of the present invention is provide highly specific monoclonal antibodies against the kringle 5 domain of apo(a). Another object of the invention is to develop an assay for Lp(a) that is not affected by the variability in size, structure and difference in glycosylation of the kringle 4 repeats of apo(a).

The present invention relates to methods for determining the amount of Lp(a) in a test sample. In one embodiment, the method comprises the steps of (a) contacting the sample and an Lp(a) specific binding agent coupled to a solid support wherein the Lp(a) specific binding agent is a monoclonal antibody or fragment thereof that specifically binds to kringle 5 of apo(a) for a time and under conditions to form binding agent-Lp(a) complexes; and (b) determining the amount of Lp(a) bound to the binding agent-Lp(a) complexes. In a preferred embodiment, the Lp(a) binding agent is a monoclonal antibody or fragment thereof which binds to substantially all Lp(a) via kringle 5 of apo(a), to plasminogen at less than 1% of Lp(a) binding and to LDL, VLDL, IDL and HDL at less than 2% of Lp(a) binding. In a more preferred embodiment, the solid support is separated from the sample before determining the amount of Lp(a) bound to the complexes. The solid support may be selected from the group consisting of nitrocellulose, latex, nylon, polystyrene, beads, particles, magnetic particles, and glass fiber. In a most preferred embodiment, the monoclonal antibody is selected from the group consisting of 1-532-266, 1-390-191, 1-458-165, 1-892-230, 1-292-189, 1-746-183, and 1-546-264.

In an alternative embodiment, the method further comprises contacting an indicator reagent to the sample and Lp(a) specific binding agent prior to step (b) above and includes the aforementioned preferred embodiments. In a preferred aspect of this embodiment, the indicator reagent is selected from the group consisting of K4 specific monoclonal antibody, K4 polyclonal antibody, K4/K5 monoclonal antibody, K4/K5 polyclonal antibody and fragments thereof.

In yet another embodiment, the invention provides a method for determining the amount of Lp(a) in a test sample comprising the steps of (a) contacting the sample, a capture reagent bound to a solid support, and an indicator reagent wherein the indicator reagent is a labeled monoclonal antibody or fragment thereof that specifically binds to kringle 5 of apo(a) for a time and under conditions to form capture reagent-Lp(a)-indicator reagent complexes; and (b) determining the amount of Lp(a) bound to the binding agent-Lp(a)-indicator reagent complexes. Alternatively, the indicator reagent is a labeled monoclonal antibody that binds to substantially all Lp(a) via kringle 5, to plasminogen at less than 1% of Lp(a) binding and to LDL, VLDL, IDL and HDL at less than 2% of Lp(a) binding. In this case, as in those mentioned above, a preferred embodiment is one which further comprises the step of separating the solid support from the sample before determining the amount of Lp(a) bound to the solid support. Preferably here, the capture reagent is selected from the group consisting of K4 specific monoclonal antibody, K4 polyclonal antibody, K4/K5 monoclonal antibody, K4/K5 polyclonal antibody and fragments thereof. Also, preferably, the indicator reagent is selected from the group consisting of 1-532-266, 1-390-191, 1-458-165, 1-892-230, 1-292-189, 1-431-378, 1-746-183, and 1-546-264.

In yet another embodiment, the invention provides a method for determining the amount of Lp(a) in a test sample comprising the steps of (a) contacting the sample, an Lp(a) specific binding agent wherein the Lp(a) specific binding agent is conjugated to a first charged substance and an indicator reagent wherein the indicator reagent is monoclonal antibody or fragment thereof that specifically binds to kringle 5 of apo(a) for a time and under conditions to form binding agent-Lp(a)-indicator reagent complexes; (b) contacting the binding agent-Lp(a)-indicator reagent complexes with an insoluble solid phase material which is oppositely charged with respect to the first charged substance, such that the solid phase material attracts and attaches to the first charged substance; and (c) determining the amount of Lp(a) bound to the binding agent-Lp(a)-indicator reagent complexes. Preferably, the first charged substance is an anionic or cationic monomer or polymer. More preferably, the indicator reagent is a labeled monoclonal antibody that binds to substantially all Lp(a) via kringle 5, to plasminogen at less than 1% of Lp(a) binding and to LDL, VLDL, IDL and HDL at less than 2% of Lp(a) binding. Even more preferably, the monoclonal antibody is selected from the group consisting of 1-532-266, 1-390-191, 1-458-165, 1-892-230, 1-292-189-1-378, 1-746-183, and 1-546-264.

In another embodiment, the invention provides a method for determining the amount of cholesterol associated with Lp(a) in a test sample comprising the steps of (a) contacting the sample and a monoclonal antibody or fragment thereof that specifically binds to kringle 5 of apo(a) wherein the antibody is coupled to a solid support; (b) separating the solid support from the sample; and (c) determining the amount of cholesterol bound to the solid support.

The invention also includes competitive assays for determining Lp(a) in a test sample. One embodiment provides a method for determining the amount of Lp(a) in a test sample comprising the steps of (a) contacting the sample and an indicator reagent wherein the indicator reagent is a monoclonal antibody or fragment thereof that specifically binds to kringle 5 of apo(a) with a solid support coated with Lp(a) for a time and under conditions to permit binding of the indicator reagent with Lp(a) in the test sample and with the Lp(a) bound to the solid support; and (b) determining the amount of Lp(a) in the test sample by detecting the reduction in binding of the indicator reagent to the solid support as compared to the signal generated from a negative sample to indicate the presence of Lp(a) in the test sample. In an alternative method, the indicator reagent is replaced by labeled Lp(a) or labeled kringle 5 of apo(a) and the bound Lp(a) is replaced by bound monoclonal antibody or a fragment thereof that specifically binds to kringle 5 of apo(a). In each instance above, a molecule bound to the solid support, whether antigen or antibody, may be bound directly or indirectly. The monoclonal antibody used in the above-described competitive assays preferably binds to substantially all Lp(a) via kringle 5, to plasminogen at less than 1% of Lp(a) binding and to LDL, VLDL, IDL and HDL at less than 2% of Lp(a) binding. More preferably, the monoclonal antibody is selected from the group consisting of 1-532-266, 1-390-191, 1-458-165, 1-892-230, 1-292-189, 1-431-378, 1-746-183, and 1-546-264.

The invention further provides a monoclonal antibody specific for Lp(a) prepared by a method comprising the steps of (a) immunizing a mouse or a rat with kringle 5 of apo(a) or a fragment thereof; (b) making a suspension of mouse or rat spleen cells; (c) fusing the spleen cells with mouse or rat myeloma cells in the presence of a fusion promoter; (d) culturing the fused cells; (e) determining the presence of anti-Lp(a) antibody in the culture media; (f) cloning a hybridoma producing antibody that binds to substantially all Lp(a), to plasminogen at less than 1% of Lp(a) binding and to other lipoproteins, such as, LDL, VLDL, IDL and HDL at less than 2% of Lp(a) binding; and (g) obtaining the antibody from the hybridoma.

The invention also includes a monoclonal antibody specific for Lp(a) wherein the antibody binds to (i) substantially all Lp(a) via kringle 5 of apo(a), (ii) plasminogen at less than 1% of Lp(a) binding and (iii) LDL, VLDL, IDL, and HDL at less than 2% of Lp(a) binding. The antibody may be an IgG or IgM isotype. A preferred IgG isotype is selected from the group consisting of 1-532-266, 1-390-191, 1-458-165 and 1-892-230. A most preferred IgG isotype is 1-892-230. A preferred IgM isotype is selected from the group consisting of 1-292-189, 1-431-378, 1-746-183, and 1-546-264. The invention also provides hybridoma cell lines that secrete the above-mentioned monoclonal antibodies.

The invention further provides a test kit for the detection and quantification of Lp(a) in a plasma sample, comprising a reagent or labeled reagent which specifically binds to kringle 5 of apo(a). dr

BRIEF DESCRIPTION OF THE FIGURES

In FIG. 2A, monoclonal antibody 1-892-230 is designated by the symbol "□", 1-532-266 by the symbol "+", 1-390-191 by the symbol "◇", and 1-458-165 by the symbol "Δ". In FIG. 2B, monoclonal antibody 1-746-183 is designated by the symbol "□", 1-292-189 by the symbol "+", 1-546-264 by the symbol "◇", and 1-431-378 by the symbol "Δ". In each plot, the antibody concentration ($\mu$g/mL) is shown on the x-axis and absorbance at 490 nm on the y-axis.

FIG. 4 shows competitive binding curves of monoclonal antibodies 1-892-230 (4A), 1-532-266 (4B) and 1-458-165 (4C) obtained by pre-incubating each antibody with a competitor, adding the mixture to the microtiter plate to which Lp(a) was already bound, and measuring the antibody bound to the Lp(a) using an ELISA.

FIGS. 5A and 5B show the binding curves for the anti-kringle 4 monoclonal antibody 4D2 and anti-apo(a) sheep polyclonal antibodies obtained by incubating these antibodies with microtiter plates coated with Lp(a) (□) LDL (+), VLDL (◇), IDL (Δ), and HDL (x) in separate wells and measuring the antibody bound to the lipoproteins using an ELISA. X- and y-axis parameters are as indicated above.

FIGS. 7A and 7B show the binding curves for HRPO-labeled anti-kringle 4 Mab (designated by the symbol "□") and anti-apo(a) [kringle 4 and kringle 5] Pab (designated by the symbol "+") to Lp(a) and kringle 5 respectively, captured by the anti-kringle 5 Mab 1-892-230 bound to microtiter plates. X- and y-axis parameters are as indicated above.

FIG. 9A compares the two assays using normal subjects and FIG. 9B uses patients as described in Example 4.

FIG. 11A compares the two assays using normal subjects and FIG. 11B uses patients as described in Example 5.

FIG. 13A compares the two assays using normal subjects and FIG. 13B uses patients as described in Example 6.

FIG. 15A compares the two assays using normal subjects and FIG. 15B uses patients as described in Example 7.

FIG. 18 shows the amino acid sequence (SEQ ID NO:1) of Kringle 5 of apo(a).

DETAILED DESCRIPTION OF THE PREFERRED EMBODIMENTS

Definitions

Figures 1A, 1B:
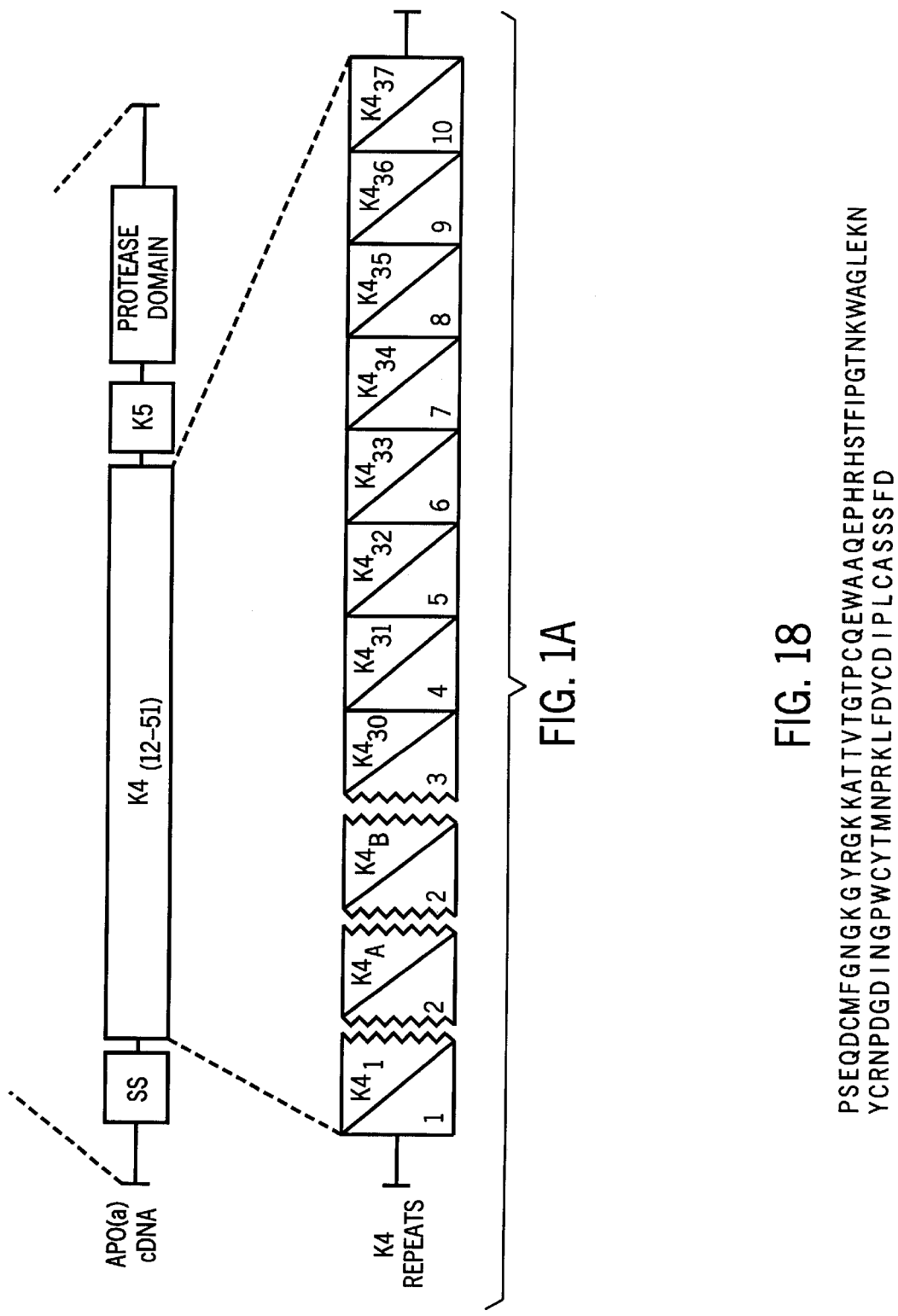
FIG. 1A is a pictorial representation of apolipoprotein (a). The apo(a) gene has four structural domains: a signal sequence (SS) which is nearly identical to that of plasminogen, a K4 region which contains 12–51 copies of the K4 repeat sequence, a single copy of kringle 5 (K5) and a protease domain. For K4 repeats, the numbers 1 through 10 represent the types of K4 structures seen.
FIG. 1B shows antibody titer plots of monoclonal antibody 1-892-230 obtained by incubating microtiter plates coated with Lp(a) (□), Kringle 5 (+), LDL (◇), VLDL (Δ), IDL (x), and HDL (∇) in separate wells, and measuring the antibody bound to the lipoproteins using an ELISA. The antibody concentration ($\mu$/mL) is shown on the x-axis and absorbance at 490 nm on the y-axis.

The term "test sample", as used herein, includes biological samples which can be tested by the methods of the present invention and include human and animal body fluids such as whole blood, serum, plasma, cerebrospinal fluid, urine, lymph fluids, and various external secretions of the respiratory, intestinal and genitorurinary tracts, tears, saliva, milk, white blood cells, and the like, biological fluids such as cell culture supernatants, fixed tissue specimens and fixed cell specimens. Any substance which can be adapted for testing with the reagents described herein and assay formats of the present invention are contemplated to be within the scope of the present invention.

The term "analyte", as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members. Analytes include but are not limited to antigenic substances, haptens, antibodies, and combinations thereof. The term "anti-analyte", as used herein, refers to an analyte specific binding member.

A "specific binding member" or "specific binding agent", as used herein, refers to one member or partner of a specific binding pair. A "specific binding pair" refers to two different molecules wherein one of the molecules through chemical or physical means specifically binds to the second molecule. A typical example of specific binding members or agents which constitute a specific binding pair are an antigen and an antibody. Other specific binding pairs can include biotin and avidin, carbohydrates and lectins, cofactors and enzymes, enzyme inhibitors and enzymes, effector and receptor molecules, and the like. Furthermore, specific binding pairs can include members that are analogs of the original specific binding members, for example, an analyte-analog. Immunoreactive specific binding members include antigens, antigen fragments, antibodies, antibody fragments, both monoclonal and polyclonal, and complexes thereof.

The term "ancillary specific binding member", as used herein, refers to a specific binding member which binds to an analyte specific binding member and includes for example, an antibody to an antibody.

The term "hapten" as used herein, refers to a partial antigen or non-protein binding member which is capable of binding to an antibody, but which is not capable of eliciting antibody formation unless coupled to a carrier protein.

A "capture reagent" as used herein, refers to an unlabeled specific binding member which is specific either for the analyte as in a sandwich assay, for the indicator reagent or analyte as in a competitive assay, or for an ancillary specific binding member, as in an indirect assay. The capture reagent can be directly or indirectly bound to a solid phase material before the performance of the assay or during the performance of the assay, thereby enabling the separation of immobilized complexes from the test sample.

An "indicator reagent" as used herein comprises a specific binding member conjugated to a label. Indicator reagents include labeled specific binding members which directly bind to analytes of interest and labeled ancillary specific binding members.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill. and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

The term "label", as used herein, refers to any substance which can be attached to specific binding agents, such as antibodies, antigens, cholesterol binding agents, Lp(a) specific binding agents and analogs thereof, and which is capable of producing a signal that is detectable by visual or instrumental means. Various suitable labels for use in the present invention can include chromogens, catalysts, fluorescent compounds, chemiluminescent compounds, radioactive elements, colloidal metallic (such as gold), non-metallic (such as selenium) and dye particles (such as the particles disclosed in U.S. Pat. Nos. 4,313,734, 4,954,452, and 4,373, 932), enzymes, enzyme substrates, and organic polymer latex particles (as disclosed in co-owned U.S. Pat. No. 5,252,459, issued Oct. 12, 1993), liposomes or other vesicles containing such signal producing substances, and the like. A large number of enzymes suitable for use as labels are disclosed in U.S. Pat. No. 4,275,149. Such enzymes include phosphatases and peroxidases, such as alkaline phosphatase and horseradish peroxidase which are used in conjunction with enzyme substrates, such as nitro blue tetrazolium, 3,5',5',5'-tetranitrobenzidine, 4-methoxy-1-naphthol, 4-chloro-1-naphthol, 5-bromo-4-chloro-3-indolyl phosphate, chemiluminescent enzyme substrates such as the dioxetanes described in U.S. Pat. No. 4,857,652 (issued Aug. 15, 1989), U.S. Pat. No. 4,931,223 (issued Jun. 5, 1990), U.S. Pat. No. 4,931,569 (issued Jun. 5, 1990), U.S. Pat. No. 4,962,192 (issued Oct. 9, 1990), and U.S. Pat. No. 4,978,614 (issued Dec. 18, 1990), and derivatives and analogs thereof. Fluorescent compounds such as fluorescein, phycobiliprotein, rhodamine and the like, including their derivatives and analogs are suitable for use as labels.

The linking of labels, i.e. labeling of peptides and proteins is well known to those of ordinary skill in the art. For example, monoclonal antibodies produced by a hybridoma can be labeled by metabolic incorporation of radioisotope-containing amino acids provided as a component in the culture medium. (See, for example, Galfre et al., (1981) Meth. Enzymol., 73: 3–46). The techniques of protein conjugation or coupling through activated functional groups are particularly applicable. (See, Avrameas et al., (1978) Scand. J. Immunol., 8(7): 7–23. Rodwell et al. (1984) Biotech., 3: 889-894 and U.S. Pat. No. 4,493,795).

The term antibody is also meant to include both intact molecules as well as fragments thereof, such as, for example, Fab and F(ab')$_2$ which are capable of binding antigen. Fab and F(ab')$_2$ fragments lack the Fc fragment of intact antibody and may have less non-specific binding than an intact antibody (Wahl, et al., J. Nucl. Med. 24: 316–325, 1983), as well as increased kinetics due to their smaller size. Such fragments also may be used for the detection and quantitation of lipoprotein cholesterol particles according to the methods disclosed herein in the same manner as intact antibodies. Such fragments are well known in the art and are typically produced by enzymatic degradation of an antibody, such as with pepsin, papain, or trypsin. Alternatively, antibodies and antibody fragments can be prepared using recombinant antibody methods such as those described in U.S. patent applications Ser. Nos. 513957, 693249, 789619, 776391, 799770, 799772, and 809083, wherein antibodies or antibody fragments are produced from the RNA of an antibody producing B-cell from an immunized animal, such as a rat, mouse, rabbit or human, using known recombinant techniques.

Kringle 5 specific binding agents according to the present invention also include bacteriophage described in U.S. Pat. No. 4,797,363. Bacteriophage tail or head segments are capable of selectively binding antigens. By mutation and selection processes, bacteriophage having the necessary binding characteristics to selectively bind lipoprotein cholesterol particles can be obtained.

Kringle 5 specific binding agents according to the present invention also include nucleic acid sequences, such as DNA and RNA, which selectively bind to Lp(a) particles. A library of nucleic acid sequences are tested for the desired binding characteristics and the sequences that are specific for lipoprotein (a) particles are isolated and replicated. Weintraub, et al., WO 92/05285, and Gold, et al., WO 91/19813, disclose methods for the preparation of DNA and RNA sequence which are antigen specific.

The Invention

The present invention provides a method for the detection and quantitation of Lp(a) in a fluid sample. A binding agent specific for a kringle 5 epitope(s) of apo(a) is used to capture intact Lp(a) particles from a fluid sample, preferably a plasma sample. The amount of Lp(a) present in the plasma sample is then determined from the amount of Lp(a) in the binding agent-Lp(a) complexes formed in the reaction. The present invention also provides reagents, such as kringle 5 specific binding agents which preferably are monoclonal antibodies, for use in the methods described herein.

The claimed method utilizes a kringle 5 specific binding agent to form a binding complex with Lp(a) particles in a sample. In one embodiment, the method is performed by combining all components of the test mixture simultaneously i.e. a binding agent specific for kringle 5 of apo(a), a test sample, and any indicator reagent(s) for detecting Lp(a)) and then determining the amount of Lp(a) present in the binding agent-Lp(a) complexes. In a second embodiment, a test sample is combined with a kringle 5 specific binding agent and then separated from the binding agent-Lp(a) complexes formed before measuring the amount of Lp(a) in the complex. Preferably, the Lp(a) particles are captured by a kringle 5 specific binding agent directly or indirectly bound to a solid support. This methodology simplifies the separation of the resulting binding agent-Lp(a) complexes.

Kringle 5 specific binding agents include kringle 5 specific binding proteins, such as monoclonal (Mab) and polyclonal antibodies (Pab) and other kringle 5 specific synthetic or recombinant proteins that specifically bind to kringle 5 of apo(a) or a part thereof (i.e. a domain). A binding agent that specifically binds kringle 5 of apo(a) will bind to substantially all Lp(a) via a kringle 5 domain of apo(a) in Lp(a) particles and will not cross-react, e.g. exhibit less than about 2% cross-reactivity with plasminogen and with other lipoprotein particles, such as LDL, very low density lipoprotein (VLDL), intermediate density lipoprotein (IDL), and high density lipoprotein (HDL). In more preferred embodiment, a kringle 5 specific binding agent is one which binds to substantially all Lp(a) via kringle 5 of apo(a), to plasminogen at less than 1% of Lp(a) binding and to LDL, VLDL, IDL and HDL at less than 2% of Lp(a) binding. In a most preferred embodiment, a kringle 5 specific binding agent exhibits no detectable cross-reactivity to other lipoproteins or to plasminogen. An antibody is a preferred kringle 5 specific binding agent and a monoclonal antibody the most preferred.

A kringle 5 specific binding agent is preferably attached directly or indirectly to a solid support, for example, by absorption, adsorption, covalent coupling directly to the support or indirectly through another binding agent (such as a second antibody), or the like utilizing methods known in the art. The type of attachment or binding will typically be dependent upon the material composition of the solid support and the type of Lp(a) specific binding agent used in the assay. For example, nitrocellulose, polystyrene and similar materials possess chemical properties that permit absorption or adsorption of proteins to a solid phase composed of this material. Other materials, such as latex, nylon, and the like contain groups that permit covalent coupling of the lipoprotein specific binding agent to the solid support. Chemical groups such as amines and carboxylic acids are coupled through the activation of the carboxylic acid group with, for example, carbodiimide compounds, to form an amide linkage. Other linking methods are well-known in the art particularly for coupling proteins to solid phases and one skilled-in-the-art can easily conceive of a variety of methods for covalently coupling the specific binding agent to the solid support. The solid support can take the form of a variety of materials, for example, the solid support may be in the form of a bead particle, a magnetic particle, a strip or a layered device.

Preferably, the specific Lp(a) particles of interest are separated from other lipoprotein particles in the sample before the determination of the amount of Lp(a) bound to the kringle 5 specific binding agent. The separation of the binding agent-Lp(a) complexes from the sample or more specifically from the other lipoprotein particles in the sample can be accomplished in a variety of ways. When the binding agent is coupled to a solid support, the solid support can be removed from the sample or the sample can be removed from the solid support. For example, when the solid support is a microtiter plate or another type of reaction well device, such as the devices described in U.S. Pat. Nos. 5,075,077 and 4,883,763, issued Dec. 24, 1991 and Nov. 28, 1989 respectively, and U.S. patent application Ser. No. 523,629, the sample can be removed from the wells and the plate washed of any residual sample. When the solid support is a particle, such as a latex or magnetic particle, the solid support can be separated from the sample by filtration through a fiber matrix, such as the devices described in U.S. Pat. No. 4,552,839, issued Nov. 12, 1985, U.S. Pat. No. 5,006,309, issued Apr. 9, 1991, EP Application 0288793, published Nov. 2, 1988, PCT Publication No. WO92/08738, published May 29, 1992, EP Patent 0424633, published Jan. 17, 1996 and Fiore et al. (1988) Clin. Chem. 34(9): 1726–1732, or by attraction to a magnet followed by removal of the particles or the sample. Alternatively, the binding agent-Lp(a) complexes can be separated or removed by filtration such as by the Ion Capture Methodology described in EP Patents 0326100 and 0406473, published Sep. 11, 1996 and Sep. 20, 1995, respectively. These applications describe the use of ion capture separation, in which specific binding members used in an assay are chemically attached to a first charged substance and a porous matrix having bound thereto a second charged substance that binds to the first charged substance. A specific binding pair is formed and separated from the reaction mixture by an electrostatic interaction between the first and second charged substances. The specific binding member is preferably covalently coupled to the first charged substance. Examples of charged substances include anionic and cationic monomers or polymers, such as polymeric acids, e.g. polyglutamic acid, polyaspartic acid, polyacrylic acid and polyamino acids; proteins and derivative proteins, such as albumin; anionic saccharides, such as heparin or alginic acid; polycations, such as GafQuat™ L-200 and Celquat™ H-100. The art is replete with examples of solid supports, as well as techniques in the separation of samples from solid supports.

Alternatively, the methods of the present invention may be performed without the need for a separation step, as described in PCT Publication No. WO94/20636, published Sep. 15, 1994. PCT Publication No. WO94/20636 teaches genetically engineered proteins, such as hybrid enzymes and their preparation and use in quantitative and qualitative assays. In the method systems described, a hybrid enzyme is provided which comprises a starting enzyme and a foreign amino acid moiety that either replaces or is inserted into an amino acid sequence of the starting enzyme at a region close to the enzyme's active site. The foreign moiety may be either a first member of a specific binding pair or a linking moiety to which a ligand may be coupled or conjugated. In either case, the resulting hybrid enzyme exhibits the enzymatic activity of the starting enzyme. Furthermore, the foreign moiety of the hybrid enzyme can still bind to its corresponding specific binding pair member or to an anti-ligand and as a consequence of such binding, modulate or modify the activity of the hybrid enzyme. Thus, in an assay system comprising a hybrid enzyme, the enzymatic activity will change depending upon the presence or the amount of analyte in the test sample.

The hybrid enzyme provides a basis for assays to detect, (1) the presence or the amount of an antibody directly or (2) the presence or the amount of an antigen indirectly by competition for binding to a binding molecule. One assay system which utilizes a hybrid enzyme comprises the steps of (1) contacting a test sample containing an analyte of interest, a hybrid enzyme capable of binding to the analyte and a binding molecule of the analyte to form a reaction mixture; (2) contacting the reaction mixture with a substrate for the starting enzyme; and (3) monitoring the change, if any, in enzymatic activity of the hybrid enzyme. As an example, in the case of an Lp(a) competitive assay, the monoclonal antibodies of the present invention may be used as a binding molecule of the analyte. Other assay formats, such as a direct assays are also envisioned. As indicated above, the manner of making hybrid enzymes and using them in competitive and direct immunoassays is fully described in WO94/20636.

The amount of Lp(a) in a plasma sample can be determined by a variety of assay formats. A preferred assay format, for example, is a sandwich assay. This method comprises contacting a test sample with a solid phase (hereinafter represented by the symbol "|-") to which at least one capture reagent (i.e. anti-analyte) is bound, to form a mixture. The mixture of test sample and capture reagent bound to a solid phase is incubated for a time and under conditions sufficient to allow |-capture reagent/analyte complexes to form. These complexes then are contacted with an indicator reagent comprising a second anti-analyte previously conjugated to a label. This second mixture is incubated for a time and under conditions sufficient for |-capture reagent/analyte/indicator reagent complexes to form. The presence of the |-capture reagent/analyte/indicator reagent complexes is determined by detecting the measurable signal generated. In such an assay, the capture reagent bound to the solid support may be, for example, a first antibody which binds to an antigen in the test sample, and the indicator reagent may be a second antibody which also binds to the antigen but at a site different from the first antibody. It is also within the scope of the present invention to use one antibody as a capture agent and a fragment of an antibody as an indicator reagent. In addition, sandwich-type assays may be configured in a reverse orientation to that described above, i.e. with an antigen serving as the capture reagent to test for the presence of antibody in a test sample. In this case, the indicator reagent is a second labeled antibody or fragment thereof which also binds to the complex of antigen/antibody bound to a solid support.

Detection of complexes formed in sandwich and other assays may be performed indirectly. In an indirect sandwich assay format, complexes of |-capture reagent/analyte/second capture reagent are formed, none of which are labeled. Instead, an ancillary specific binding member which binds to the second capture reagent acts as the indicator reagent. For example, when the second capture reagent is a mouse antibody to the analyte of interest, the complex of capture reagent/analyte/mouse antibody may be detected using an ancillary antibody which is labeled, such as labeled goat anti-mouse antibody. Furthermore, the use of biotin and antibiotin, biotin and avidin, biotin and streptavidin, and the like, may be used to enhance the generated signal in the assay systems described herein.

For purposes of illustration, the following sandwich formats may be utilized: in a first format, Lp(a) particles present in a plasma sample are specifically captured by a kringle 5 specific monoclonal antibody immobilized on a solid support. After removing the other lipoprotein particles, the Lp(a) bound to the solid support is quantitated using a labeled anti-kringle 4 monoclonal antibody as an indicator reagent. A second format uses similar capture phase technology as in format 1 above, but the detection antibody in the sandwich is instead an anti-apo(a) polyclonal antibody that is directed towards both kringle 4 and kringle 5 domains of apo(a). In a third format, Lp(a) particles present in a plasma are captured by a kringle 4 specific monoclonal antibody immobilized on a solid support. After washing away the other lipoprotein particles, the Lp(a) bound to the solid support is quantitated using a labeled anti-kringle 5 specific monoclonal antibody. In a fourth format, an anti-apo(a) kringle 4 monoclonal antibody bound to a support is used to capture Lp(a) particles and the detection antibody is a polyclonal labeled antibody, directed towards both kringle 4 and kringle 5 domains. In yet another format, Lp(a) particles are specifically captured by a kringle 5 specific monoclonal antibody and the bound Lp(a) is detected by another kringle 5 monoclonal antibody with different epitope specificity, as described in the present invention. Preferably, in these formats, the indicator reagent is labeled with an enzyme.

Alternatively, a kringle 5 specific binding agent can be used in a sandwich immunoassay method for the quantitation of Lp(a)-cholesterol in a plasma sample. This involves the specific capture of the Lp(a) particles in the plasma sample by the kringle 5-specific antibody immobilized on the solid support followed by quantitation of cholesterol in the captured Lp(a) particles by a cholesterol binding agent which is coupled directly or indirectly to a label. The Lp(a)-cholesterol bound cholesterol binding agent is then quantitated by detection and measurement of the label. Methods for determining cholesterol associated with lipoproteins are well known to those of ordinary skill in the art. (See for example, PCT Publication No. WO93/18067, published Sep. 16, 1993).

In addition to the foregoing sandwich assay formats, competitive assays are also contemplated by the invention. In one format, labeled Lp(a) may compete with the Lp(a) to be determined in the plasma sample for binding to a kringle 5 specific monoclonal antibody which has been immobilized on a solid support. In a second format, Lp(a) may be attached to a solid support, and then incubated with a fixed amount of kringle 5 monoclonal antibody added to a sample suspected of containing Lp(a). The amount of kringle 5 which binds to the Lp(a) on the solid support may then be determined using a labeled antibody which binds to the kringle 5 antibody, for example, an anti-mouse labeled antibody. In a third format, the Lp(a) in the sample competes with Lp(a) attached to the solid support for binding by a labeled kringle 5 antibody. It is fully expected that other known assay formats may be advantageously adopted by the skilled artisan and these are within the scope of the invention, to be utilized with the unique antibodies herein set forth and described.

Another alternative is based on an immunochromatographic assay format (such as described in U.S. Pat. No.

4,954,452 and U.S. Pat. No. 5,229,073, for example) in which the lipoprotein particles in the test sample bind to a labeled Lp(a) binding agent. The resulting complexes then travel along a test strip by capillary action. The labeled Lp(a) complexes are then captured by a high affinity anti-Lp(a) specific antibody immobilized on the test strip, followed by detection and measurement of the captured labeled Lp(a) complexes. Typically, the test strip is comprised of a porous or bibulous membrane and the result is determined by a visual readout of a detectable signal. Other test strip assay formats are also within the scope of the invention.

The use of scanning probe microscopy (SPM) for immunoassays also is a technology to which the monoclonal antibodies of the present invention are easily adaptable. In scanning probe microscopy, in particular in atomic force microscopy, in the capture phase, for example, at least one of the monoclonal antibodies of the invention is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. Such a system is described in Publication No. WO 92/15709, published Sep. 17, 1992.

The use of SPM to monitor specific binding reactions can occur in many ways. In one embodiment, one member of a specific binding pair (described below) is attached to a surface suitable for scanning. The attachment of the specific binding member may be by adsorption to a test piece comprising a solid phase of a plastic or metal surface, using methods known to those of ordinary skill in the art.

Alternatively, a specific binding member may be covalently (i.e. irreversibly) attached to a test piece, in which case the test piece comprises a solid phase of derivatized plastic, metal, silicon, or glass. Covalent attachment methods are also known to those skilled in the art. If the test piece is silicon or glass, the surface must be activated prior to attaching the specific binding member. Activated silane compounds such as triethoxy amino propyl silane (available from Sigma Chemical Co., St. Louis, Mo.), triethoxy vinyl silane (Aldrich Chemical Col, Milwaukee, Wis.) and (3-mercapto-propyl)-trimethoxy silane (Sigma Chemical Co., St. Louis, Mo.) can be used to introduce reactive groups such as amino-, vinyl-, and thiol-, respectively. Such activated surfaces can be used to link the binding member directly (in the cases of amino or thiol) or the activated surface can be further reacted with linkers such as glutaraldehyde, bis (succinimidyl), SPPD 9 succinimidyl 3-[2-pyridyldithio] propionate), SMCC (succinimidyl-4-[N-maleimidomethyl] cyclohexane-1-carboxylate), SIAB (succinimidyl-[4-iodoacetyl] aminobenzoate, and SMPB (succinimidyl 4-[1-maleimidophenyl]butyrate) to separate the binding member from the surface. The vinyl group can be oxidized to provide a means for covalent attachment. It also can be used as an anchor for the polymerization of various polymers such as polyacrylic acid, which can provide multiple attachment points for specific binding members. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons), all of which are available from Pharmacia, Piscataway, N.J., or Ficoll (molecular weight 70,000 daltons), available from Sigma Chemical Co. Also, polyelctrolyte interactions may be used to immobilize a specific binding member on a surface of a test peice by using techniques and chemistries described supra in the Ion Capture methodology. Attachment by covalent means is a preferred method.

Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Also included as part of the invention are immunoassay kits for the detection and quantification of Lp(a) in a patient sample which includes one or more of the heretofore described labeled reagents and capture reagents. For example, it is contemplated that the reagent employed for the assay can be provided in the form of a kit with one or more containers such as vials or bottles, with each container containing a separate reagent such as a monoclonal antibody, or a cocktail of monoclonal antibodies, employed in the assay. These kits also could contain vials or containers of other reagents needed for performing the assay, such as washing, processing and indicator reagents.

The following examples are illustrative of the invention and are in no way to be interpreted as limiting the scope of the invention as defined in the claims. It will be appreciated that one skilled-in-the-art can conceive of many other devices and methods for use of which the present inventive concepts can be applied. Throughout the entire specification, it is intended that citations to the literature (whether patents, patent applications or articles) are expressly incorporated by reference.

GENERAL METHODOLOGIES

1. Development of Anti-Kringle Monoclonal Antibodies

Peptide sequences of the kringle 4 repeats and the single kringle 5 domain in apo(a) are well known (Eaton et al. (1987) Proc Natl Acad Sci 84: 3224–3228; McLean et al. (1987) Nature (London) 330: 132–137). Recently, Li et al. have expressed and purified kringle 4 in *Escherichia coli* (Li et al. (1992) Protein Express Purification 3: 212–222). A recent report describes the expression of a recombinant kringle 5 of human apo(a) (Chevinesse et al (1996) Protein Expression and Purification 8: 145–150). Kringle 5 of apo(a) containing 101 peptide residues [SEQ ID NO:1 and also shown as residues 4204–4294 of FIG. 1 of McLean et al. (1987) supra] was expressed as a fusion protein with maltose binding protein in *Escherichia coli*. The fusion protein was first purified from whole cell lysate by amylose agarose affinity chromatography, then cleaved to release kringle 5 protein which was purified by fast flow liquid chromatography (Pharmacia). The purified samples of kringle 5 and kringle 5-fusion protein were used for monoclonal antibody production.

a. Immunization:

Six female 4–6 week old BALC/c mice (Charles River, Wilmington Mass.) were immunized with the kringle 5 fusion protein of lipoprotein (a) (Lp(a)) at week 0, 4, 8, 16, and 20. The dose level was 12.5 mg in 0.1 mL using a 1:1 ratio of the kringle 5 fusion protein with RIBI adjuvant (RIBI Immunochem Research, Inc, Hamilton, Mont.). The adjuvant emulsion route of injection was equally distributed interperitoneally and subcutaneously. Three days prior to the fusion, mice were given an immunization of 12.5 mg Kringle 5 fusion protein via intersplenic injection.

b. Sera Evaluation:

Ten days following the fifth immunization, sera samples were taken by retro-orbital vein puncture. Sera samples were analyzed for Lp(a) specific antibody titer by enzyme immunoassay (EIA). Microtiter wells were coated with 100 mL of Lp(a) at 1 mg/mL in phosphate buffered saline (PBS) or 100 mL PBS and incubated at room temperature overnight. The following day the plates were blocked for 30 minutes with 200 mL per well of 3% v/v fish gelatin (Norland Products Inc., New Brunswick, N.J.) in PBS. After washing the plate, 50 mL of serum was added per well, at log 2 serial dilutions starting at a 1:100 dilution, and incubated 1 hour. The plates were washed and 50 mL of diluted goat anti-mouse IgG+ M-HRPO (Kirkegaard and Perry Laboratories, Gaithersburg, Md.), was added per well to the plate for a 30 minute incubation period. The plate was washed a final time and the substrate o-phenylenediame 2HCI (OPD) (Abbott Laboratories, Abbott Park, Ill). was added to develop the color. The relative intensity of optical density readings identified mouse number 2 & 6 to have the highest Lp(a) titer with minimal non-specific reactivity and these mice were selected for fusion twenty nine weeks following the first immunization.

c. Fusion:

On the day of fusion, the two mice were euthanized by cervical dislocation and a splenectomy was performed. Splenocytes were flushed out and washed in Iscoves's Modified Dulbecco's Medium (IMDM) (GIBCO, Grand Island, N.Y.) and centrifuged at 1000 rpm for 5 minutes. The splenocytes were combined with SP2/0 myeloma cells at a 2:1 ratio, washed in IMDM, and centrifuged. The supernatant was removed and 1 mL of 50% polyethylene glycol (PEG) (American Type Culture Collection, Rockville, Md.) was added to the pellet for one minute as the pellet was gently dispersed by tapping and swirling. Thirty mLs of IMDM were added to the mixture and centrifuged as previously described. The supernate was decanted and the pellet resuspended in IMDM with HAT (Hypoxanthine Aminopterin Thymidine) (GIBCO, Gaithersburg, Md.), 15% Fetal Bovine Serum (FBS) (Hyclone Laboratories, Logan, Utah.), Origen Hybridome Cloning Factor (Igen, Rockville, Md.), and *Salmonella typhimurium* mitogen (STM) (1% v/v) (RIBI Immunochem Research, Inc., Hamilton, Mont.). The fused cells were plated into 96 well tissue culture plates at $3\times10^5$ cells per well. The cell culture media was changed by aseptically aspirating half the tissue culture supernate and feeding with IMDM with 1% v/v HT (hypoxanthine and thymidine) Supplement (GIBCO, Gaithersburg, Md.), and 10% v/v FBS at days five and seven. The fusion protocol was referenced from Galfre, G. and Milstein, C. (1981). Preparation of Monoclonal Antibodies: Strategies and Procedures, Meth Enzymol 73: 1–46.

d. Fusion Screening:

The primary screening of the fusion occurred on day ten with confluent cultures. An EIA was run similar to the assay used to test sera samples. Microtiter wells were coated with 100 mL of 1 mg/mL Lp(a) in PBS and incubated at room temperature overnight. After washing and blocking, as previously described, 50 mL of culture supernate was added and incubated 1 hour. The plates were washed and goat anti-mouse HRPO conjugate was added to each well. This was followed by washing and color development with OPD. The relative intensity of optical density readings identified hybrids 1-292, 1-390, 1-431, 1-458, 1-532, 1-546, 1-746, & 1-892 as 3 times that of negative control, normal mouse serum (NMS) (Organon Teknika-Cappel, Malvern, Pa.). These hybrids were then expanded. All the above listed hybrids were retested using the same EIA format described previously.

These hybrids were selected for cloning because the optical density readings indicated specific binding to Lp(a) with minimal nonspecific binding.

e. Hybrid Cloning:

Hybrids 1-292, 1-390, 1-431, 1-458, 1-532, 1-546, 1-746 and 1-892 were cloned by limiting dilutions starting at 1:100, 10-fold to $10^6$. The cloning media used was IMDM with 10% v/v FBS and 1% v/v HT Supplement. A 200 mL cell suspension was added to each of the 96 wells in the TC plate.

f. Clone Selection:

The clone screening occurred on day ten with confluent cultures. Clones 1-292-189, 1-390-191, 1-431-378, 1-458-165, 1-532-266, 1-546-1-892-230 were selected based on EIA reactivity specific to Lp(a) with minimal non-specific binding. The EIA screening protocol used was as described previously.

g. Isotypes:

The isotypes of the monoclonal antibodies secreted from the cell lines identified above were determined using an EIA clonotyping kit (Southern Biotech, Birmingham, Ala.). The assay was performed according to the manufacturer's recommendations and the results are shown below.

| Monoclonal | Type | Monoclonal | Type |
| --- | --- | --- | --- |
| 1-292-189 | IgM kappa | 1-390-191 | IgG3 kappa |
| 1-431-378 | IgM kappa | 1-458-165 | IgG2a kappa |
| 1-546-264 | IgM kappa | 1-532-266 | IgG2a kappa |
| 1-746-183 | IgM1 kappa | 1-892-230 | IgG1a kappa | h. Antibody Production:

Cell lines with an IgG isotype were expanded in tissue culture flasks using IMDM with 5% v/v Fetal Calf Serum (Hyclone Laboratories, Logan, Utah.) at a cell density between $1\times10^4$ cells/mL and $5\times10^5$ cells/mL until they could be expanded into roller bottles. The cells were allowed to grow in the roller bottles for maximum antibody production, normally until viability fell below 5%.

Cell lines with an IgM isotype were expanded in tissue culture flasks with IMDM with 5% v/v Fetal Calf Serum at a cell density between $1\times10^4$ cells/mL and $5\times10^5$ cells/ml, with viability >90%. These cells were used for ascites production in BALB/c mice as described by Brodeur et al., Production of monoclonal antibodies in mouse ascites, in *Monoclonal Antibody Production Techniques and Applications* (L. Schook, ed.), Marcel Dekker, Inc., New York, 1987, pp. 99–111.

i. Antibody Purification:

Cultures were removed from roller bottles and the cells were allowed to settle for three days at 4–8° C. Cell supernate was filtered through a 0.45 mm filter and concentrated approximately 20-fold using an Amicon Concentrator, (Amicon Corp., Beverly, Mass.). The concentrated supernate was filtered through an additional 0.45 mm filter. This material was then purified by Protein A Sepharose column chromatography as described by Ey et al., "Isolation of Pure IgG1, IgG2a, and IgG2b immunoglobulins from Mouse Serum using Protein A Sepharose", Immunochem 15: 429–436 (1978). The purified and dialyzed antibody was tested for Lp(a) reactivity by EIA as previously described.

Ascites fluid was filtered through a 0.22 mm filter and purified by gel filtration on a Sephacryl S-300 (Pharmacia LKB, Piscataway, N.J.) sizing column as described by Bouvet et al., "A Modified Gel Filtration Technique Producing Unusual Exclusion Volume IgM: a Simple Way of Preparing Monoclonal IgM" Journal of Immunological Methods 66: 299–305 (1984). The purified antibody was tested for Lp(a) reactivity by ELISA as previously described.

Figure 1B:
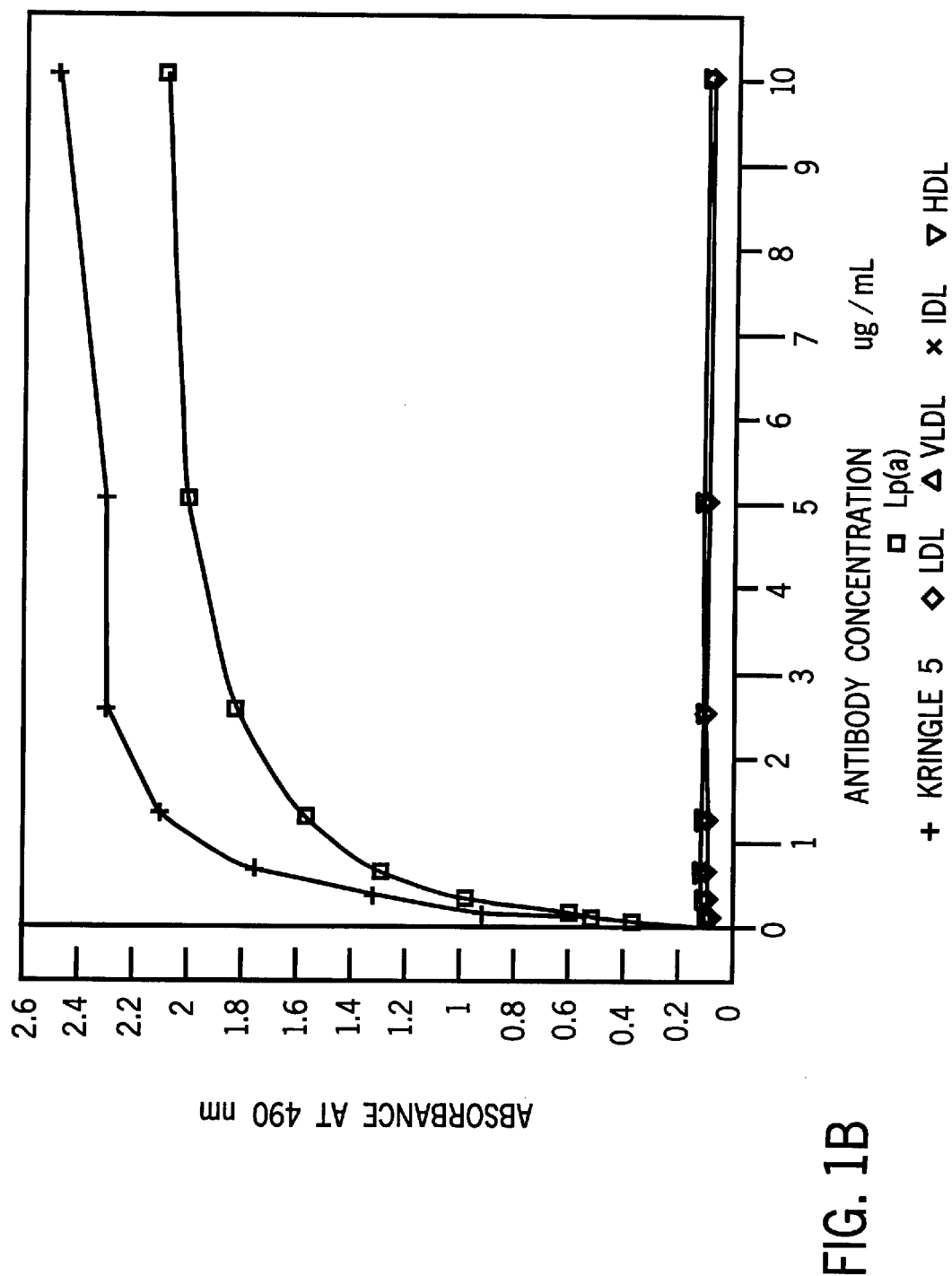
Figure 2A:
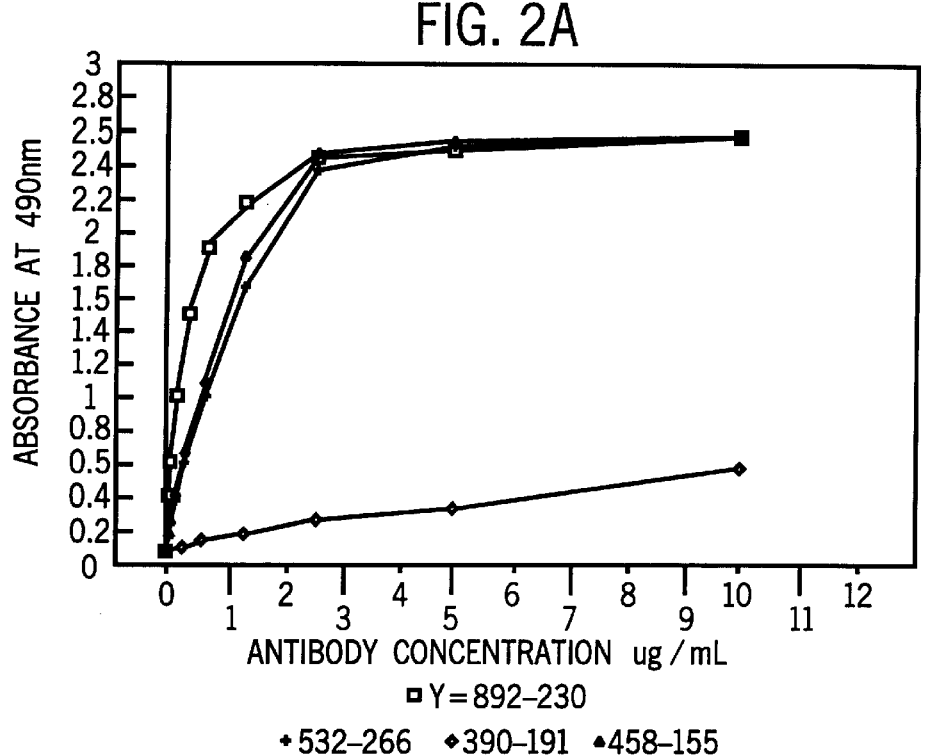
FIGS. 2A and 2B are antibody titer plots of four IgG and four IgM monoclonal antibodies, respectively, obtained by incubating these antibodies with Lp(a) bound to microtiter plates and measuring their binding using an ELISA.
Figure 2B:
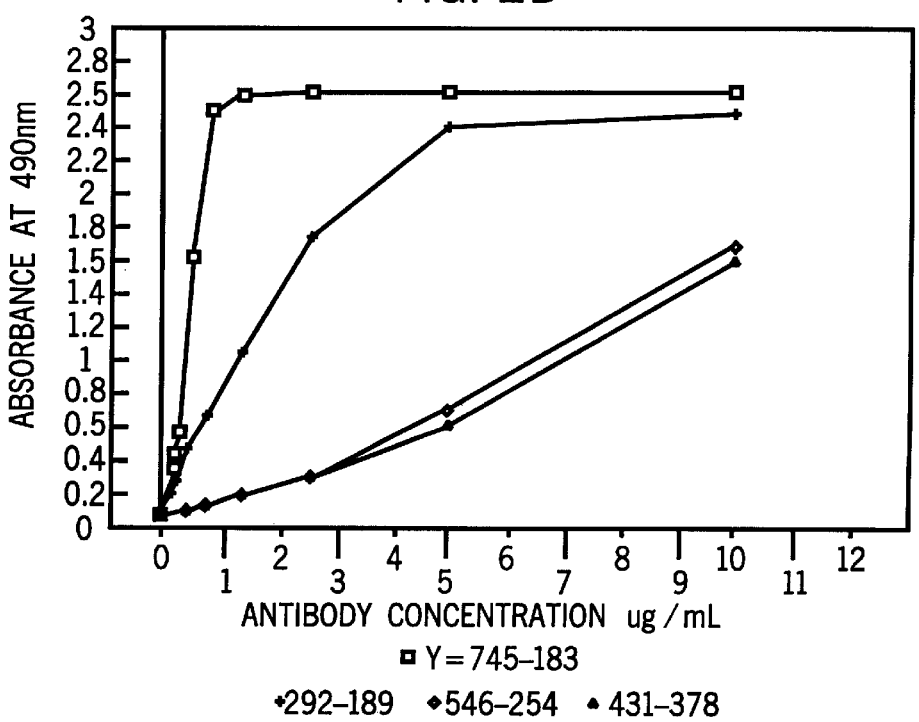

2. Evaluation of the Monoclonal Antibodies a. Direct ELISA Using Lipoprotein and Kringle 5 Coated Microtiter Plates:

Lipoprotein fractions (LDL, HDL, VLDL, IDL, and Lp(a)), purified by ultracentrifugation (see Example 2, infra), and purified kringle 5, obtained from Dr. Gunther Fless of the University of Chicago, were coated on separate wells of a Maxisorb Nunc Immuno Plate as follows: one hundred microliters (100 mL) of each lipoprotein fraction at a lipoprotein-cholesterol concentration of about 1 mg/mL and 1 mg/mL of kringle 5 in 20 mM phosphate buffered saline, pH 7.0 (PBS) were dispensed into separated wells of the microtiter plate. The plate was incubated at 37° C. for one hour, then washed five times with PBS containing 0.05% (v/v) Tween 20 (PBS-Tween 20). The non-specific binding sites were blocked by incubating 200 mL of 10% (v/v) fetal bovine serum (FBS) in PBS in each well at 37° C. for one hour and then the wells were washed five times with PBS-Tween 20. Each Mab was diluted in 3% (v/v) FBS in PBS to a final antibody concentration of about 2 mg/mL and the diluted Mab solutions were then serially diluted in the reaction wells of the plate. After incubation at 37° C. for one-half hour, the plate was washed five times with PBS-Tween 20. Thereafter one hundred microliters (100 mL) of horseradish peroxidase (HRPO) labeled goat anti-mouse IgG+IgM (obtained from Kirkegaard and Perry Laboratories, Md.), diluted in 3% FBS in PBS to a final concentration of about 1.25 mg/mL, were added to each reaction well and the plate was incubated at 37° C. for one-half hour. The plate was then washed eight times with PBS-Tween 20. One hundred microliters (100 mL) of freshly prepared HRPO substrate solution, containing one o-phenylenediamine (OPD) tablet per five milliliters (5 mL) of citrate buffer, pH 6 (both available from Abbott Laboratories, Ill.), were added to each well. The color reaction was stopped after five minutes by adding 100 mL of IN $H_2SO_4$ to the reaction wells. An absorbance reading of each reaction well was then obtained with a Bio-Tek microplate reader at 490 nm. Typical binding curves for each lipoprotein and kringle 5 tested with Mab 1-892-230 are shown in FIG. 1. As can be seen from these binding curves, the Mab binds only to Lp(a) and kringle 5 and not to any other lipoproteins. FIGS. 2A and 2B show a comparison of the binding of four selected IgG Mabs and four selected IgM Mabs developed against the kringle 5 immunogen. The results show that three IgG Mabs 1-892-230, 1-532-266 and 1-458-165 have similar reactivities for Lp(a). In the IgM Mab series, Mab 1-746-183 showed higher reactivity for Lp (a) when compared to 1-292-189, and much higher reactivity than the other two Mabs.

b. Direct ELISA Using Mab-Coated microtiter Plates:

Mabs were coated onto the reaction wells of microtiter plates after dilution of the Mabs in PBS as follows: IgG Mabs 1-892-230, 1-532-266, 1-390-191 and 1-458-165 were each diluted to a concentration of 20 mg/mL; IgM Mabs 1-746-183, 1-546-264, 1-431-378 and 1-292-189 were each diluted to concentration of 50 mg/mL. One hundred microliters (100 mL) of each Mab solution were dispensed into separate reaction wells and incubated at room temperature on a rotator at 100 rpm for two hours. The plates were than washed five times with PBS-Tween 20 and blocked with 200 mL of 10% FBS in PBS by incubation at 37° C. for one hour. The plates were then washed five times with PBS-Tween 20.

Figure 3:
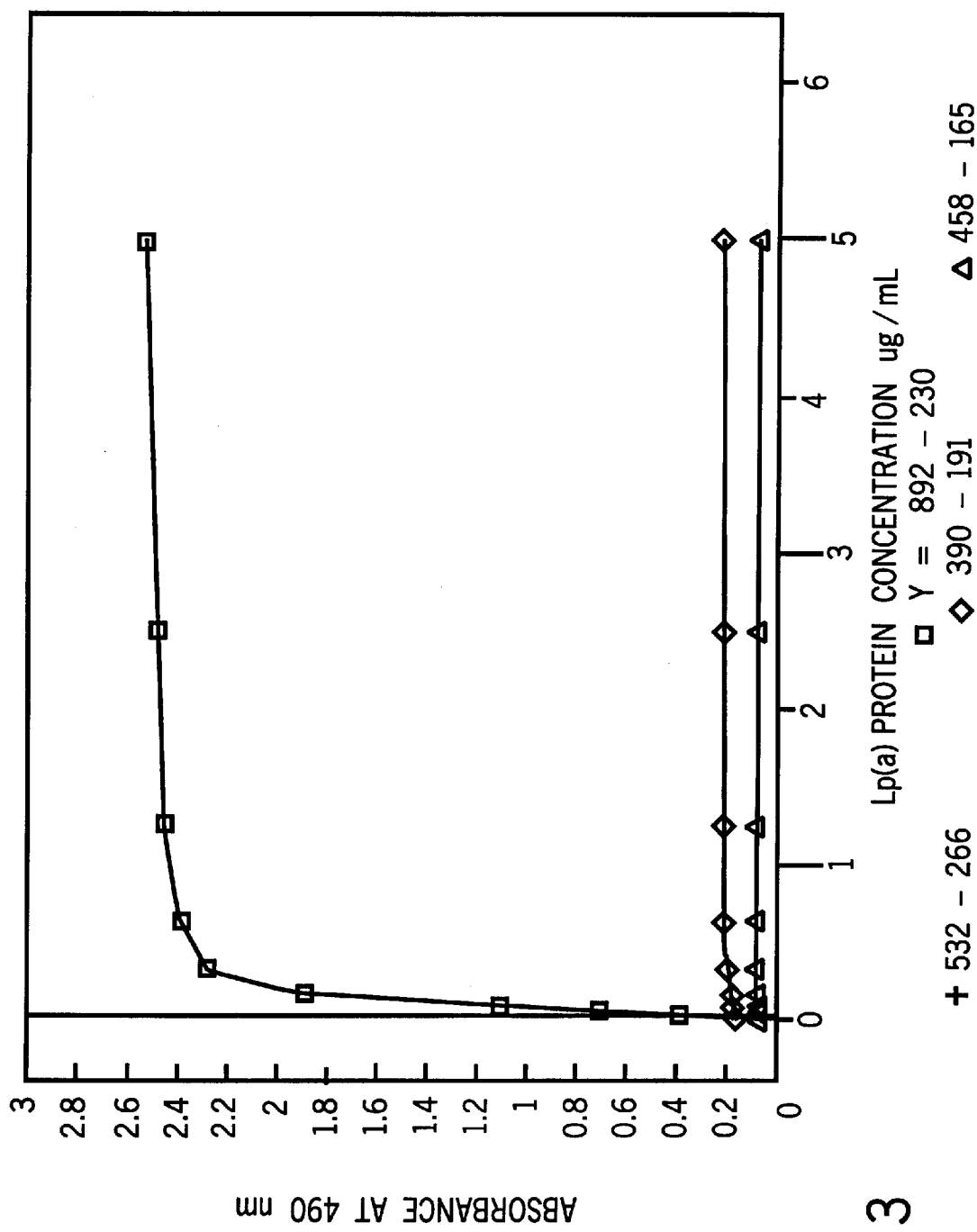
FIG. 3 shows titration curves of Lp(a) with four IgG monoclonal antibodies obtained by measuring the binding of Lp(a) to microtiter plates which have been coated with the monoclonal antibodies. The monoclonal antibodies and their symbol designations as well as the x- and y-axis parameters are the same as in FIG. 2A above.
Figure 4A:
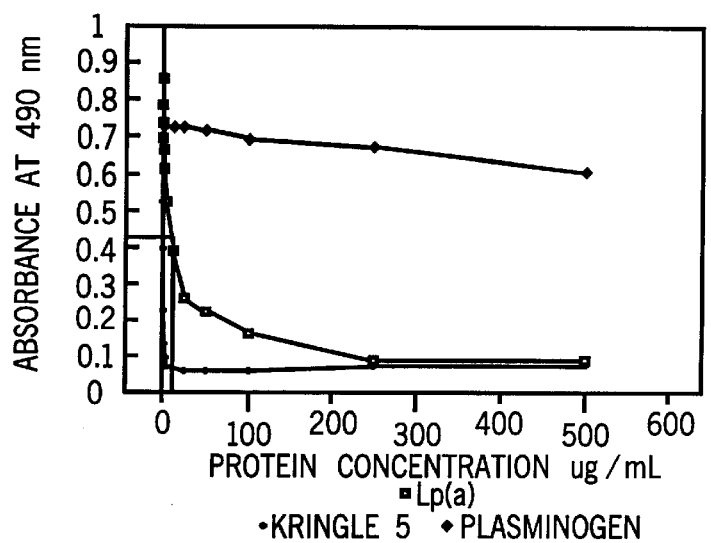
In FIGS. 4A, 4B, and 4C, Lp(a) is designated by the symbol "□", kringle 5 by the symbol "+", and plasminogen by the symbol "◇". X- and y-axis parameters are as indicated above.
Figure 4B:
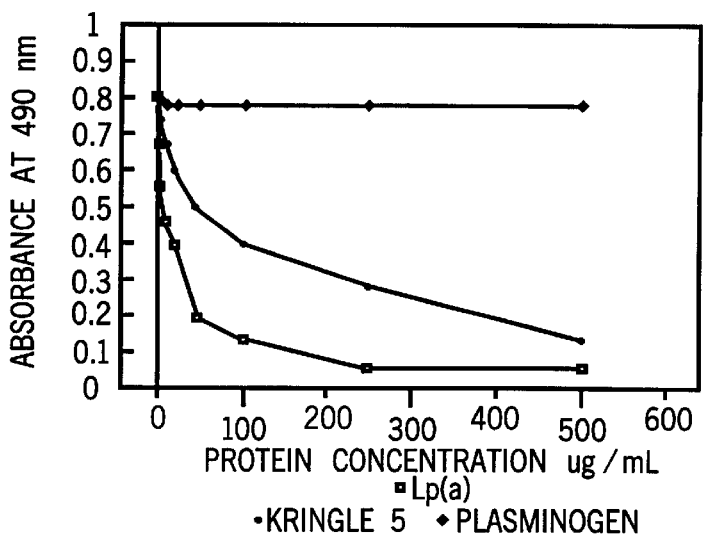
Figure 4C:
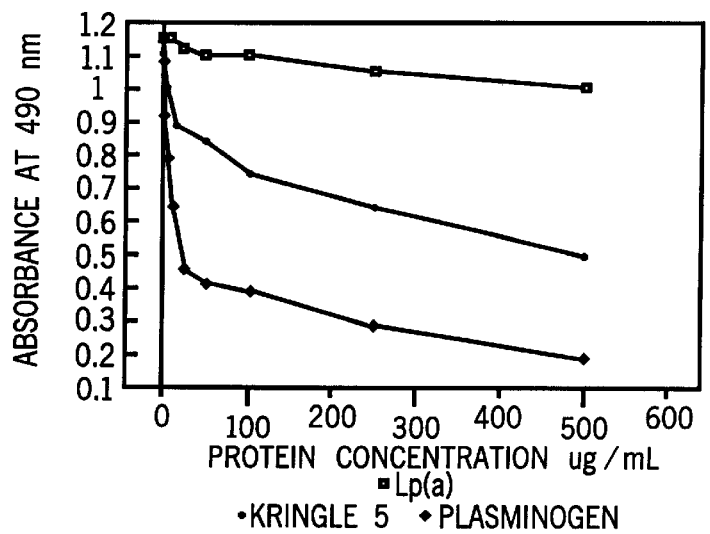
Figure 6:
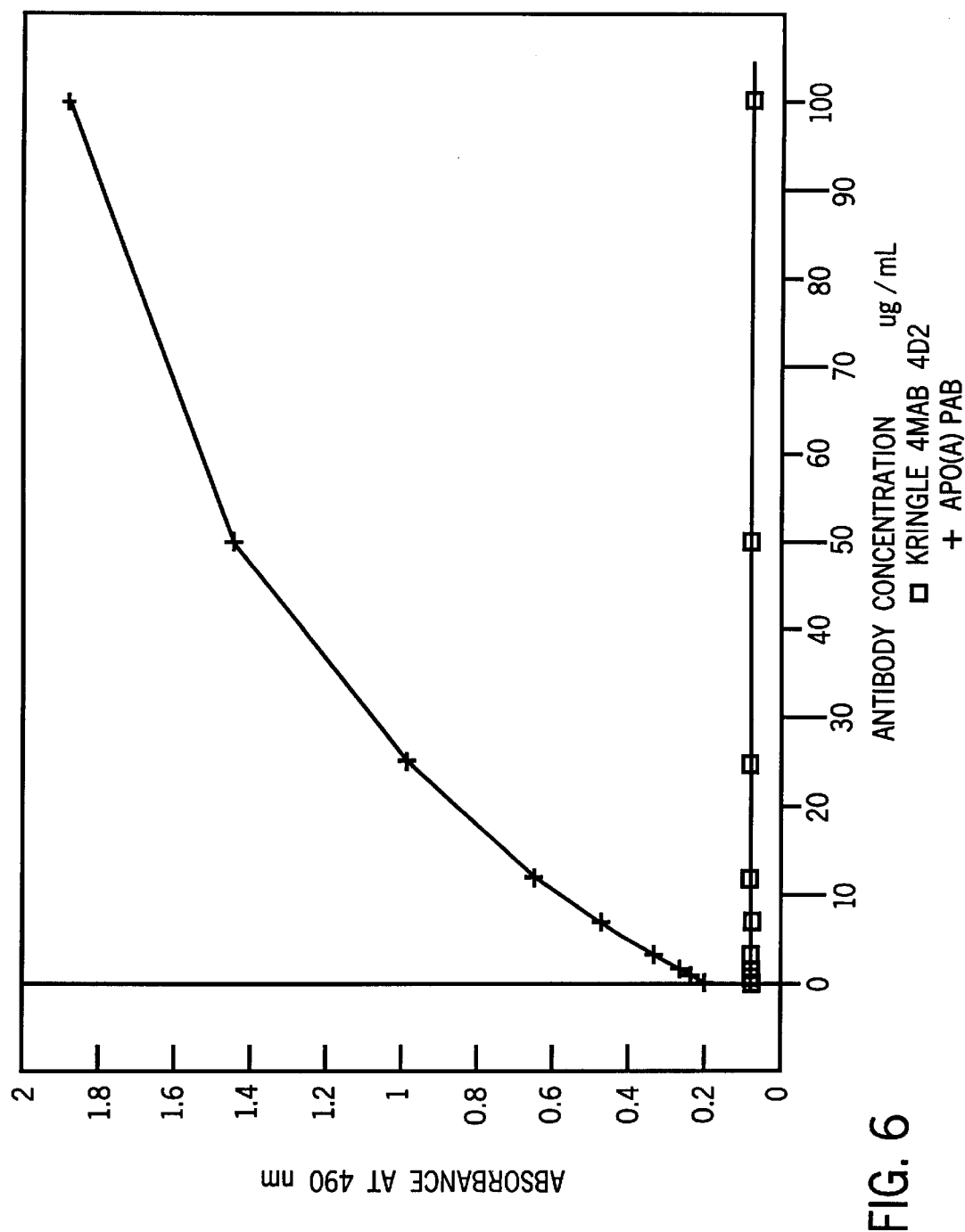
FIG. 6 shows direct binding curves of the anti-kringle 4 monoclonal antibody (Mab) 4D2 and anti-apo(a) sheep polyclonal antibody (Pab) bound to kringle 5 coated on the microtiter plates. In the Figure, monoclonal antibody is designated by the symbol "□" and polyclonal antibody by the symbol "+". X- and y-axis parameters are as indicated above.
Figure 8:
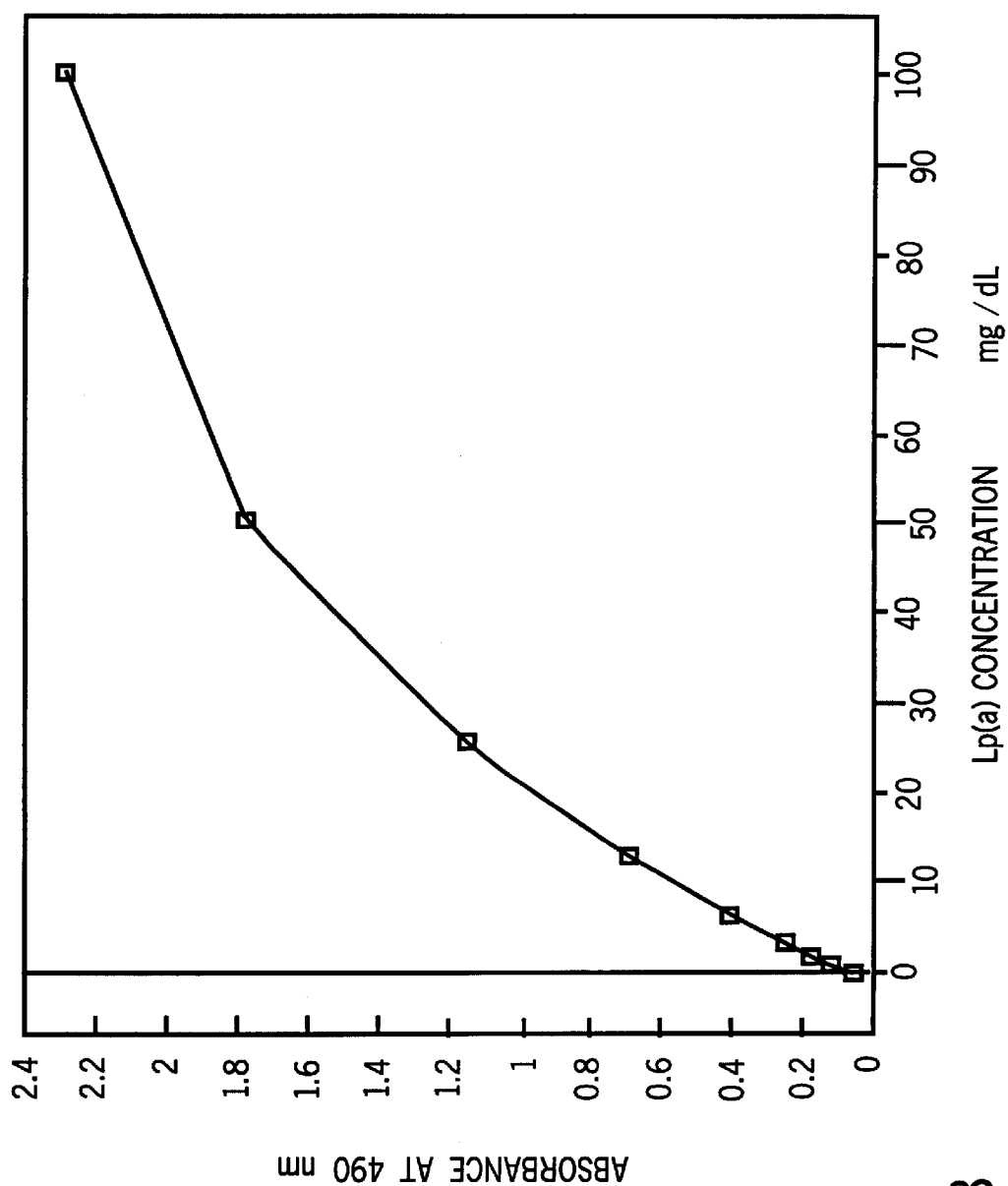
FIG. 8 shows a calibration curve of Lp(a) concentration in mg/dL (x-axis) versus absorbance at 490 nm (y-axis) using anti-kringle 5 as the capture antibody and HRPO-labeled anti-kringle 4 Mab for detection as described in Example 4.

Lp(a) was then serially diluted in PBS into each Mab plate, starting with an Lp(a) protein concentration of 5 mg/mL, so that each well contained a total of 100 mL of solution. After incubation at 37° C. for one-half hour, the plates were washed five times with PBS-Tween 20. One hundred microliters (100 mL) of 0.5 mg/mL Mab 4D2-HRPO or 5 mg/mL sheep Pab-HRPO conjugate (prepared according to Example 3) in 3% FBS in PBS were added to each well and incubated at 37° C. for one-half hour. (The specificitites of both labeled Abs are discussed in section 2d. below.) HRPO substrate was added and the absorbance measured as described in section 2a above. The results indicated that among the IgG Mabs only the Mab 1-892-230 gave a positive reaction, as shown in FIG. 3. None of the four IgM Mabs reacted in this assay format. It should be noted that some of these same IgG and IgM Mabs did bind to Lp(a) when Lp(a) was immobilized on the solid phase as described in section 2a above and FIGS. 2A and 2B. Thus, the reactivity of some Mabs towards Lp(a) is dependent on whether the reaction is done on a solid phase or in a fluid phase.

c. Specificity of the Antibodies for Lp(a) Using Lipoprotein Coated Microtiter Plates in Competitive Assays:

The specificities of three selected IgG Mabs, 1-892-230, 1-532-266 and 1-458-165 were determined by competitive binding of the Mabs to Lp(a), kringle 5 and plasminogen (American Diagnostica) in microplate wells coated with Lp(a). The Lp(a)-coated plates were prepared as described previously (see Section 2a above). Each Mab was diluted with 3% (v/v) FBS in PBS to a concentration that was two times the Mab concentration at 50% Lp(a)-binding, as determined from the binding curves prepared in section 2a above. Examples of such curves are shown in FIG. 2. Purified Lp(a), kringle 5 and plasminogen at starting concentrations of 1mg/mL in PBS each, were serially diluted with PBS in reaction wells previously blocked with 10% (v/v) FBS in PBS. To each of these wells were added 50 mL of the diluted Mab solutions. The Mab-competitor mixtures were incubated at room temperature for one-half hour on a rotator at 100 rpm. The contents from each well were then transferred to Lp(a)-coated reaction wells and the plates were incubated at 37° C. for one-half hour. The amount of Mab bound to the Lp(a)-coated reaction wells was measured according to the method described in section 2a above. The binding curves of the three IgG Mabs are shown in FIGS. 4A, 4B and 4C. The inhibition curves for the Mab 1-892-230 in FIG. 4A indicate that the binding of this Mab to Lp(a) can be inhibited by kringle 5 and by Lp(a) but not by plasminogen. The inhibition curves for the Mab 1-532-266 in FIG. 4B indicate that the binding of this Mab to Lp(a) can be inhibited better by Lp(a) than by kringle 5 and not at all by plasminogen. On the other hand, the binding of Mab 1-458-165 to Lp(a) cannot be inhibited by Lp(a) itself, but is very effectively inhibited by plasminogen and weakly inhibited by kringle 5. From these inhibition studies, it can be inferred that the above three IgG Mabs do not have the same reactivity with and may not be directed to the same epitope (s) of kringle 5. The Mab 1-458-165 is possibly directed towards an epitope that recognizes plasminogen better than kringle 5. The Mab 1-532-266 is possibly directed towards an epitope of kringle 5 that is more accessible on Lp(a) than kringle 5. Thus, the Mab 1-892-230 appears to be an ideal Mab for our purposes because of its inhibition by both kringle 5 and Lp(a).

d. Selection of Antibodies that Specifically Bind to Kringle 4 and Kringle 4/Kringle 5:

Monoclonal antibodies specific for the kringle 4 domain were developed in our laboratory (see U.S. Pat. No. 5,229, 073; Li et al. (1992) Protein Express Purification 3: 212–222). FIG. 5A shows the binding curves of one of these Mab, 4D2. Polyclonal antibody against apo(a), which is purified by adsorption with an LDL-Sepharose gel to remove unwanted cross-reactive antibodies, was selected for detection of both kringle 4 and kringle 5 domains of apo(a). The binding curve of this Pab is shown in FIG. 5B. To illustrate the binding of the above two antibodies with the kringle 5 domain of apo(a), the following experiment was performed: Kringle 5 (1 mg/mL) in PBS was coated onto the wells of a microtiter plate and then the wells were blocked with 10% (v/v) FBS as described in Section 2a above. The anti-kringle 4 Mab 4D2 and the anti-apo (a) Pab were then serially diluted starting at 100 mg/mL. The experiment was completed as previously described in section 2a except that the wells containing Mab 4D2 received HRPO-labeled goat anti-mouse IgG (Kirkegaard and Perry Laboratories, Md.) and the wells containing Pab anti-apo (a) received HRPO-labeled rabbit anti-sheep IgG, both at a concentration of 0.5 mg/mL in 3% (v/v) FBS in PBS. The binding curves of the two antibodies are shown in FIG. 6. The results demonstrate that Mab 4D2 does not bind to kringle 5, indicating that its previously defined specificity against the kringle 4 domain has no cross-reactivity with the kringle 5 domain, and that polyclonal anti-apo(a) binds to kringle 5 as well as the previously shown binding to kringle 4.

e. Binding of Anti-kringle Antibodies to Lp(a) and Kringle 5 Captured by Anti-Lp(a) antibodies: The anti-kringle 4 Mab 4D2 and the anti-apo(a) Pab as described above were selected to confirm that the Mab 1-892-230 binds to the kringle 5, and not the kringle 4, domain of apo(a). For this purpose, the two antibodies were labeled with HRPO as described in Example 2. The experiment was performed as follows: Mab 1-892-230 (20 mg/mL) was coated onto the wells of microtiter plates and then the wells were blocked as described in section 2c above. In one plate Lp(a), and in the other plate, purified kringle 5 were serially diluted starting at 10 mg/mL. After incubation at 37° C. for one hour, the plates were washed five times with PBS-Tween 20. One hundred microliters (100 mL) of HRPO-labeled anti-kringle 4 Mab 4D2 (0.5 mg/mL) or HRPO-labeled anti-apo(a) Pab (5 mg/mL) in 3% (v/v) FBS in PBS were added to respective wells in each plate. The remainder of the procedure was as described in section 2b above.

The results are shown in FIGS. 7A and 7B. FIG. 7A shows that Lp(a) containing both kringle domains binds to anti-kringle 4 Mab and anti-apo(a) Pab labeled Abs using anti-kringle 5 Mab as the capture Ab, confirming both kringle 4 and kringle 5 specificities. On the other hand, the kringle 5 captured by Mab 1-892-230 as shown in FIG. 7B reacts only with labeled anti-apo(a) Pab with kringle 4 and kringle 5 specificities, but not with lableled anti-kringle 4 Mab 4D2. The above experiment thus confirms that the Mab 1-892-230 is directed against an epitope of kringle 5 and does not recognize kringle 4. On the basis of this experiment as well as those described in Section 2a and 2b, Mab 1-892-230 was selected as the best choice to develop an epitope specific Lp(a) assay.

3. Lp(a) Binding Agents a. Lp(a) Standards:

Lp(a) standards were prepared from purified Lp(a) samples (described in Example 3 infra) by diluting in 3% (v/v) FBS in PBS for immunoassays or in 1% alkali-treated casein in PBS for sandwich assays. The Lp(a)-protein concentrations were determined and were multiplied by 4.21 to get total Lp(a) as described by Fless et al. (1989) J. Lipid Res. 30: 651–662).

b. Preparation of Digitonin-Peroxidase Conjugates for Lp(a)-Cholesterol:

Three parts of a digitonin solution (2.5 mg/mL in water) (Sigma Chemical Company, St. Louis, Mo.) were mixed with one part of a fresh solution of sodium meta-periodate (1.68% w/v periodate in water) at 4° C. for one hour and then the mixture was dialyzed against 20 mM PBS, pH 8.0 overnight at 4° C. One part of a solution of 0.25 mM ethylenediamine in 20 mM PBS, pH 8.0 was added to four parts of the dialyzed mixture and the mixture was incubated at 4° C. After 30 minutes, and again after 60 minutes of incubation, 100 mL of a sodium borohydride solution (4 mg/mL in 0.1 N NaOH) was added to the mixture for each 30 mg of digitonin in the mixture. The mixture was then incubated for two hours at 4° C. The resulting mixture containing ethylenediamine derivatized digitonin was dialyzed against 0.01 M carbonate buffer, pH 9.5, at 4° C. overnight. The final carbonate buffer solution of ethylenediamine derivatized digitonin contained about 1.5 mg digitonin/mL buffer.

Twenty-five milligrams of horseradish peroxidase (HRPO) (155 Ku/mg, commercially available from Amano International) were dissolved in 6.25 mL of water, and 1.25 mL of a freshly prepared solution of 0.2 M sodium meta-periodate was added. After 20 minutes in the dark at room temperature, the mixture was dialyzed against 4 liters of 1 mM acetate buffer, pH 4.5, at 4° C. for 4 hours. The oxidized HRPO solution and the ethylenediamine derivatized digitonin solultion were mixed and stirred in the dark at room temperature for two hours. Then 400 mL of a sodium borohydride solution (4 mg/mL in water) was added and the reaction was incubated at 4° C. After two hours, the mixture was dialyzed against 20 mM PBS, pH 7.4 at 4° C. overnight. To the dialyzed reaction mixture, fatty acid free bovine serum albumin (BSA) (Sigma Chemical Company) was added to a final concentration of 5 mg/mL. The solution of HRPO-digitonin conjugate was sterile filtered through a 0.22 micron filter (Coaster Labs) and stored at -20° C.

c. Preparation of Peroxidase Conjugates of Anti-Lp(a) Antibodies:

Horseradish peroxidase (155 Ku/mg, Amano International) was dissolved in water (250 mL) and oxidized with freshly prepared 0.2 M sodium m-periodate (50 mL) at room temperature in the dark for 20 minutes. The oxidized peroxidase was then dialyzed against 2 liters of 1 mM acetate buffer (pH 4.5) at 4° C. for four hours. Two mg/mL each of monoclonal antibodies against kringle 4 (4D2), against kringle 5 (1-892-230) or polyclonal antibody against apo(a) were dialyzed against 0.01 M carbonate buffer (pH 9.5) at 4° C. and each was titrated with 20 mL of 0.2 M carbonate buffer (pH 9.5). The antibody and the dialyzed peroxidase were then mixed at room temperature in the dark for two hours. To this mixture 24 mL of freshly prepared sodium borohydride (Aldrich, 4 mg/mL in water) was added and then incubated at 4° C. in the dark for two hours. The peroxidase-antibody conjugate was then dialyzed against two liters of 20 mM PBS, pH 7.4 at 4° C. and stored at –20° C. in small aliquots.

EXAMPLE 1

Preparation of Lipoprotein Fractions (LDL, VLDL, IDL and HDL)

Blood samples from normal fasting subjects were collected into ethylenediamine-tetraacetic acid (EDTA) and the red blood cells were removed by centrifugation. The plasma samples were then analyzed for Lp(a) using the TERUMO ELISA kit (TERUMO Medical Corp., Elkton, Md.). Plasma samples containing less than 1 mg/dL Lp(a)cholesterol were selected to use for the purification of VLDL, IDL, LDL. and HDL. Lipoprotein subfractions were prepared in a Beckman Ultracentrifuge with a SW 40 Ti rotor by successive ultracentrifugation at 4° C. (Havel et al. (1955) *J. Clin. Invest.* 34: 1345–1355). VLDL was collected at a density of about 1.0006 g/mL; IDL was collected at a density range of about 1.006–1.019 g/mL; LDL was collected at a density range of about 1.019–1.050 g/mL; and HDL was collected at a density range of about 1.080–1.255 g/mL. All fractions were isolated by a tube-slicing technique. The lipoprotein fractions were dialyzed exhaustively against 0.15 M sodium chloride containing 0.1% EDTA and 0.1% sodium azide, pH 7.4 at 4° C. IDL, LDL and HDL fractions were sterile filtered through 0.2 micron and VLDL through 0.45 micron membrane filters (Nalgene) and stored at 4° C.

EXAMPLE 2

Plasma Samples

The lipid profiles of 116 plasma samples from patients with no known cardiac problems (#1–39), cardiac patients who are taking lipid-lowering drugs (#40–78) and diabetic patients (#79–116) are shown in Table 1. Total cholesterol, HDL-cholesterol and triglycerides were measured using an Abbott Vision® instrument and reagents (Abbott Laboratories, Abbott Park., Ill. LDL-cholesterol (Friedewald) was calculated using the standard equation used in the art as: [LDL-cholesterol]=[Total-cholesterol]–[HDL-cholesterol]–Triglyceride/5]. LDL-cholesterol was also determined by ultracentrifugation-precipitation (Beta-quantitation) by ultracentrifugation of a plasma sample at 40,000 rpm for 20 hours at a density of 1.006 gm/mL, removing the upper VLDL layer, measuring the cholesterol and HDL-cholesterol concentrations using the Abbott Vision® instrument and reagents, and calculating as follows: [LDL-cholesterol]=[infranet-cholesterol]–[HDL-cholesterol]. The Lp(a) concentrations were determined using a commercial ELISA for Lp(a) (TERUMO Medical Corp., Elkton, Md.).

EXAMPLE 3

Preparation of Lp(a) Standards and Calibrators

Lp(a) concentrations in fresh plasma samples were measured using a commercial ELISA for Lp(a) (TERUMO Medical Corp., Elkton, Md.). Plasma samples with high Lp(a) concentrations were ultracentrifuged for 20 hours at 40,000 rpm at a density of 1.080 g/mL. The upper lipoprotein fraction containing Lp(a), LDL, VLDL and IDL was dialyzed and then the Lp(a) was affinity purified on a Lp(a) specific monoclonal antibody (4F2) Sepharose 4B column as described in U.S. Pat. No. 5,229,073. The purity of the Lp(a) obtained from the column was determined by polyacrylamide gel electrophoresis (PAGE) under denaturing conditions, by SDS-PAGE under reducing conditions and by Western Blot. The protein content of the Lp(a) obtained from the column was measured using a Lowry assay and the cholesterol concentration was measured using the Abbott Vision® Cholesterol Assay (Abbott Laboratories, Abbott Park, Ill. Lp(a) standards and calibrators were prepared from purified Lp(a) in 3% (v/v) FBS in PBS for immunoassays and in 1% alkali-treated casein in PBS for sandwich assays.

EXAMPLE 4

Figure 10:
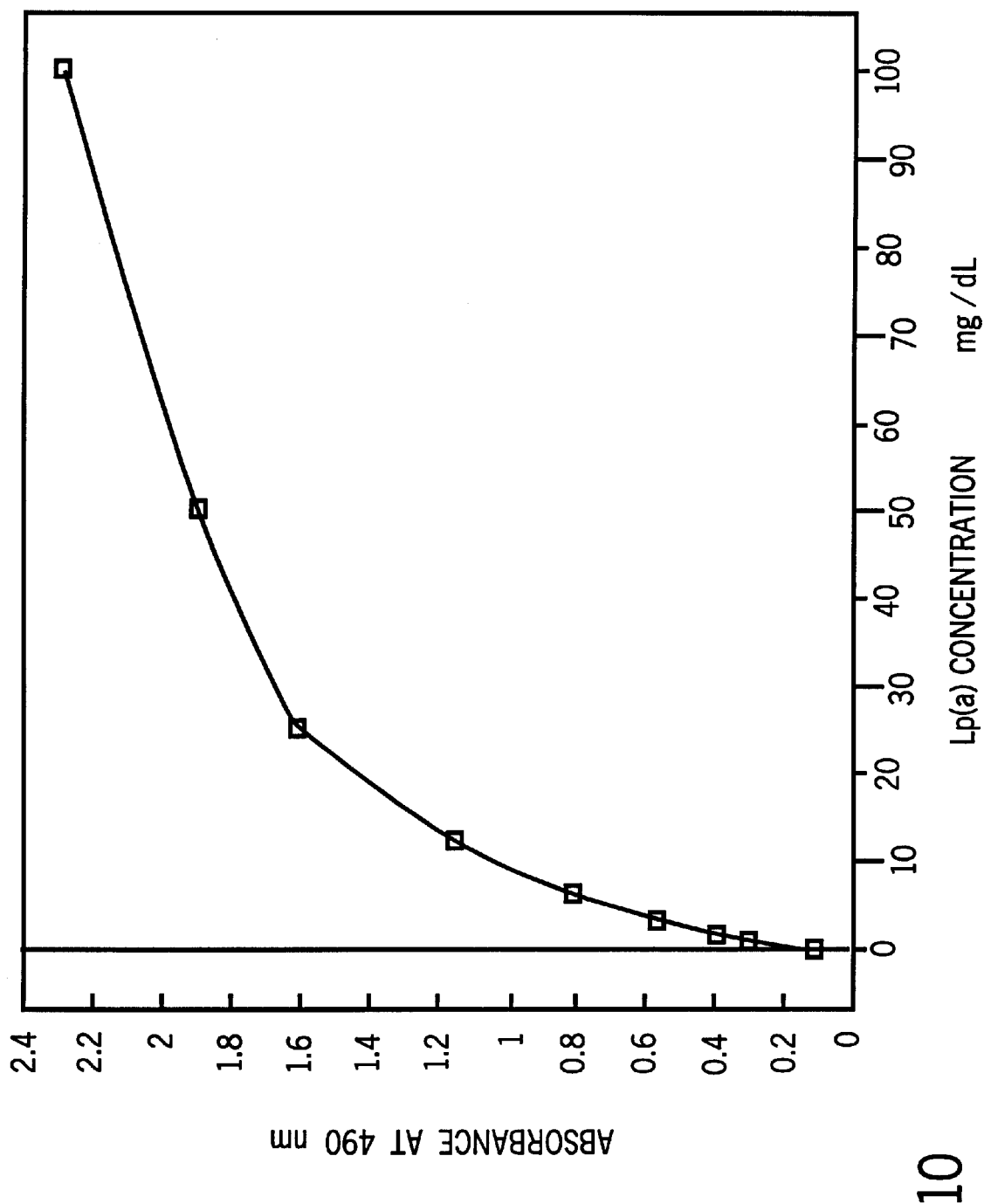
FIG. 10 shows a calibration curve of Lp(a) concentration concentration in mg/dL (x-axis) versus absorbance at 490 nm (y-axis) using anti-kringle 5 Mab as the capture antibody and HRPO-labeled anti-apo(a) Pab for detection as described in Example 5.

Lp(a) Immunoassay with Anti-Kringle 5 Mab as Capture and HRPO-Labeled Anti-Kringle 4 Mab for Detection a. Anti-kringle 5 Coated Plates:

The kringle 5 specific Mab 1-892-230 was diluted in 20 mM PBS, pH 7.4, to a final concentration of 1.25 mg/mL. One-hundred microliters of the solution were added to each well of Maxisorb Nunc Immuno plates and incubated at room temperature with gentle shaking for two hours. The plates were washed five times with PBS-Tween and then blocked with 200 mL/well of 10% (v/v) FBS in 20 mM PBS by incubation at 37° C. for one hour. The plates were stored at 4° C. with plastic sealers. Before use, the plates were washed five times with PBS-Tween.

b. Lp(a) Standard Curves:

Lp(a) standards were prepared as described in Example 3 above. Calibrators having 0, 0.0195, 0.039, 0.078, 0.156, 0.312, 0.624, 1.248 and 2.5 mg/mL were prepared by serial dilution of the 2.5 mg/mL solution made from a Lp(a) standard in 3% (v/v) FBS in 20 mM PBS at pH 7.4. One-hundred microliters of Lp(a) standards (in duplicate) were incubated in the anti-kringle 5 coated plates, prepared as described above, at 37° C. for one hour. After washing the plates five times with PBS-Tween, 100 mL of anti-kringle 4 Mab 4D2-HRPO conjugate (prepared as described in Section 3c above) at 0.25 mg/mL in 3% FBS in PBS was added to each well and incubated at 37° C. for one hour. The plates were washed with PBS-Tween eight times. The enzyme substrate o-phenylenediamine (OPD) (100 mL of a standard solution prepared from one OPD tablet/10 mL citrate buffer, pH 6; both commercially available from Abbott Laboratories, Abbott Park, Ill. was added to the wells. After incubation for 5 minutes, the color reaction was stopped with 100 mL of 1 N sulfuric acid. The plates were read at 490 nm on a microplate reader (Bio-Tek). The Lp(a) concentrations were multiplied by 400 to generate the standard curves because the plasma samples would be diluted 400 fold prior to performing the assay. A plot of Lp(a) concentration versus absorbance was prepared from the resulting data. FIG. 10 is illustrative of such a plot.

c. Lp(a) Immunoassay:

Plasma samples were diluted 400-fold with 3% w/v FBS in 20 mM PBS, at pH 7.4. One-hundred microliters of the diluted samples were added to each well of the kringle 5 coated plates and the plates were incubated at 37° C. for one hour. After washing the plates five times with PBS-Tween, 100 mL of anti-kringle 4 Mab 4D2-HRPO conjugate (0.25 mg/mL in 3% w/v FBS in 20 mM PBS, pH 7.4) were added to each well. The plates were incubated at 37° C. for one hour and then washed ten times with PBS-Tween. One-hundred microliters of a freshly prepared solution of o-phenylenediamine in citrate buffer (prepared as above) were added to each well and after five minutes the reaction was quenched with 100 mL of 1 N sulfuric acid. The absorbance of each well was measured on a Bio-Tek microplate reader at 490 nm. The Lp(a)-cholesterol concentration for each sample was then determined from a standard curve of absorbance versus Lp(a)-cholesterol concentration, prepared as described above. The calibrators and the plasma samples were assayed on the same plate to minimize the effect of variations in the reagents, materials or conditions.

Figure 9A:
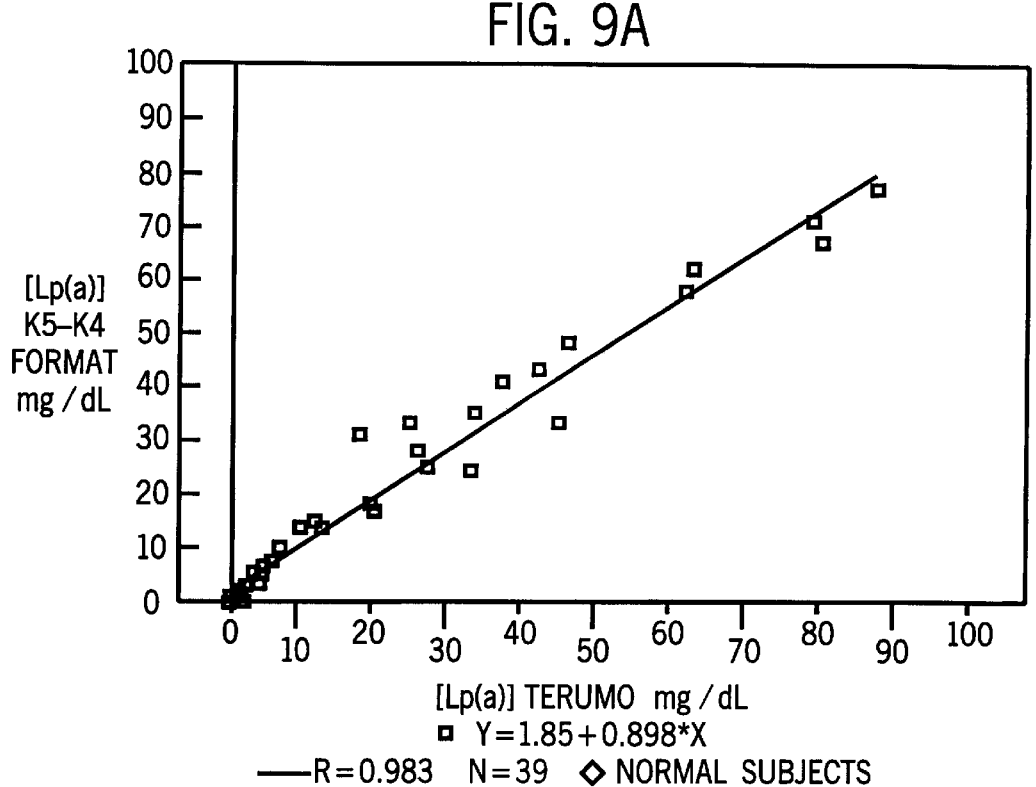
FIGS. 9A and 9B show correlation curves for Lp(a) assays using anti-kringle 5 Mab 1-358-230 as the capture antibody and HRPO-labeled anti-kringle 4 Mab 4D2 for detection (y-axis) vs. the Terumo ELISA (x-axis).
Figure 9B:
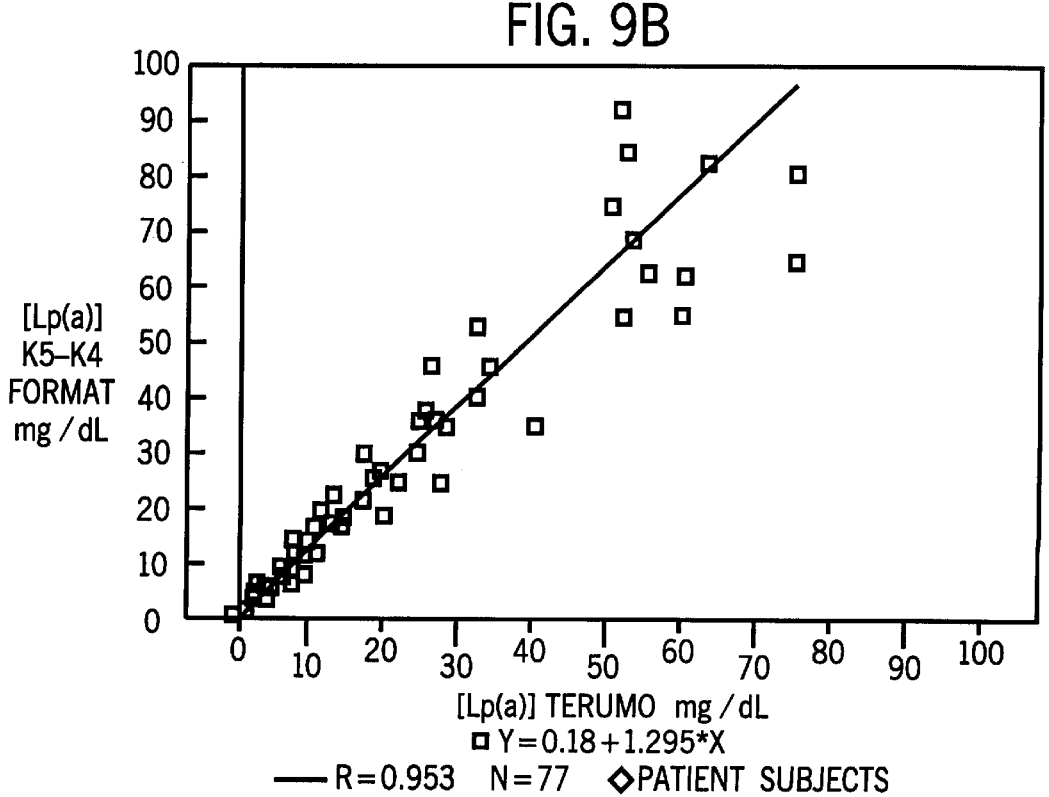

The Lp(a) concentrations of the samples determined using a TERUMO ELISA for Lp(a) (TERUMO Medical Corp., Elkton, Md.) and the method described above are shown in Table 2. The results in Table 2 illustrate the excellent correlation between the TERUMO ELISA method and the present method for determining Lp(a) levels in normal subjects (FIG. 9A) [correlation coefficient (r)=0.983; slope=0.898; intercept=1.85). The results obtained by the present method showed an excellent correlation with the TERUMO ELISA method (r=0.953, intercept=0.18) but the slope was 1.29 (FIG. 9B) on cardiac and diabetic patients. However, the TERUMO ELISA tended to produce erroneous results for the cardiac and diabetic patients, especially those with Lp(a) concentrations >50 mg/dL. The lower Lp(a) values seen using the TERUMO ELISA method were not surprising because of the assay's upper limit of 80 mg/dL Lp(a) and the slope of the standard curve above 50 mg/dL Lp(a).

EXAMPLE 5

Lp(a) Immunoassay with Anti-Kringle 5 Mab as Capture and HRPO-Labeled Anti-APO(A) Pab for Detection The preparation of the anti-kringle 5 plates, the generation of the Lp(a) standard curves and the Lp(a) immunoassay were performed exactly in the same way as described in Example 4 except that HRPO-labeled anti-apo(a) Pab conjugate was used instead of HRPO-anti-kringle 4 conjugate. The concentration of HRPO-anti-apo(a) conjugate, prepared as described in Section 3c, used was 1 mg/mL.

Figure 11A:
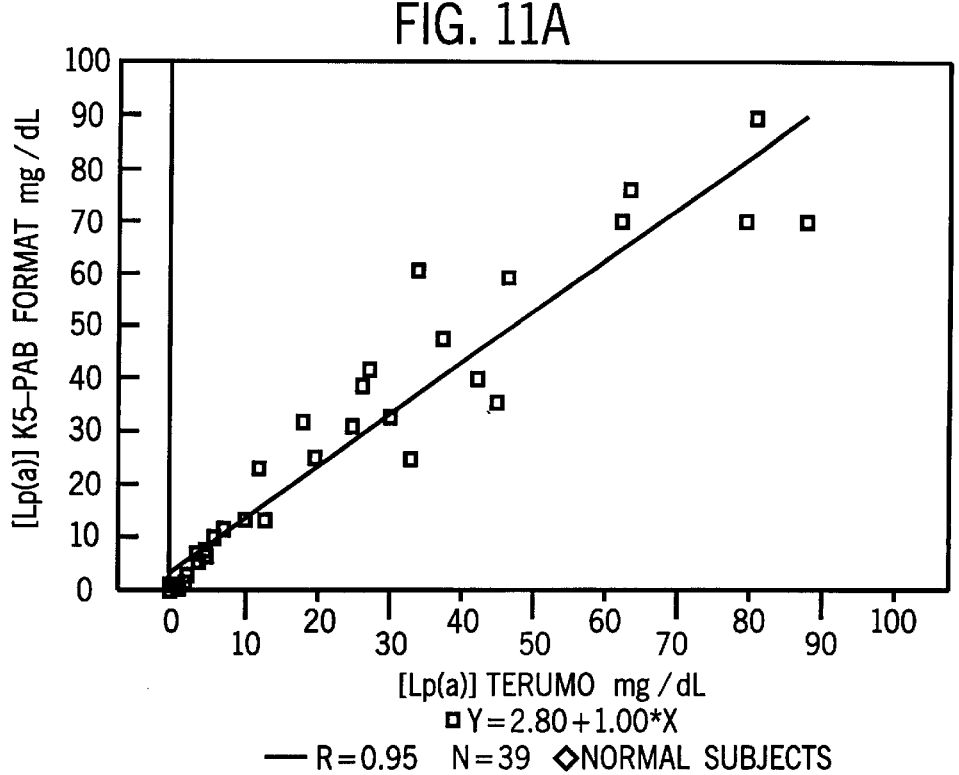
FIGS. 11A and 11B show correlation curves for Lp(a) assays using anti-kringle 5 Mab 1-892-230 as the capture antibody and HRPO-labeled anti-apo(a) Pab for detection (y-axis) vs. the Terumo ELISA (x-axis).
Figure 11B:
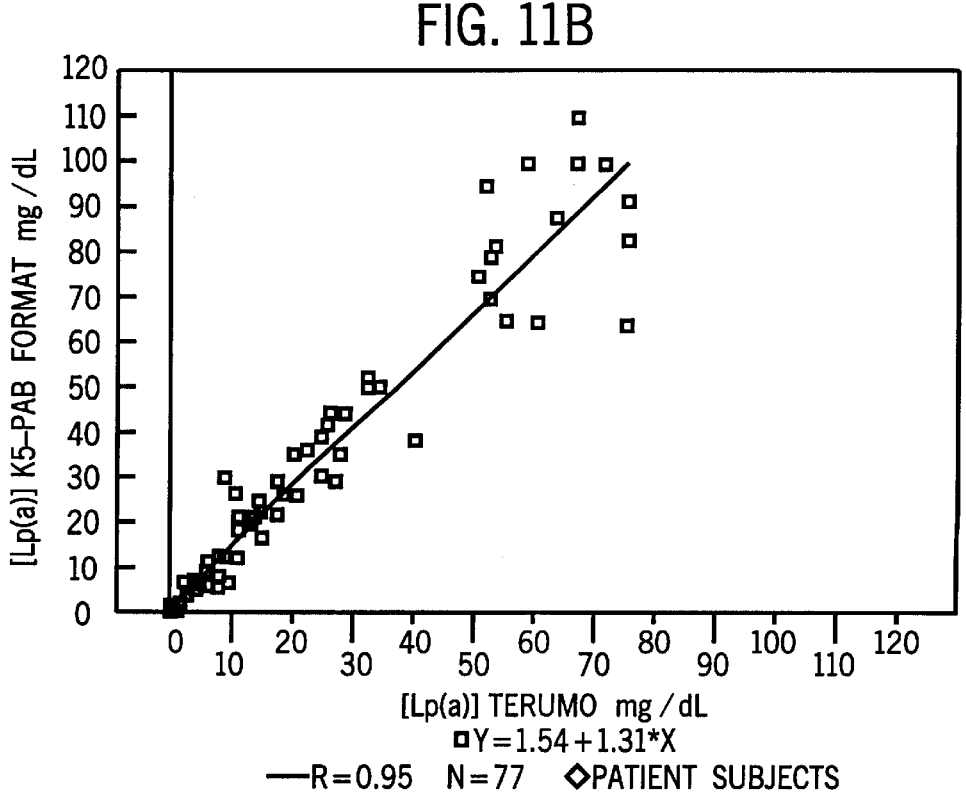

A typical standard curve is shown in FIG. 10. The results of the Lp(a) assay are presented in Table 2 and the correlation between the Lp(a) concentrations measured by the TERUMO ELISA and the present format are shown in FIG. 11A and 11B. Excellent correlation between the TERUMO ELISA method and the present method was obtained in normal subjects (FIG. 11A) [r=0.95; slope=2.80; intercept= 1.00]. On the other hand, the correlation between the two methods in cardiac patients and diabetic subjects (FIG. 11 B) showed results similar to those observed in Example 4 above. The correlation between these methods in the patient population were: correlation coefficient (r)=0.95; intercept= 1.54; slope=1.31. The observed high slope in this format is attributed to explanations similar to those discussed in Example 4c above.

EXAMPLE 6

Figure 12:
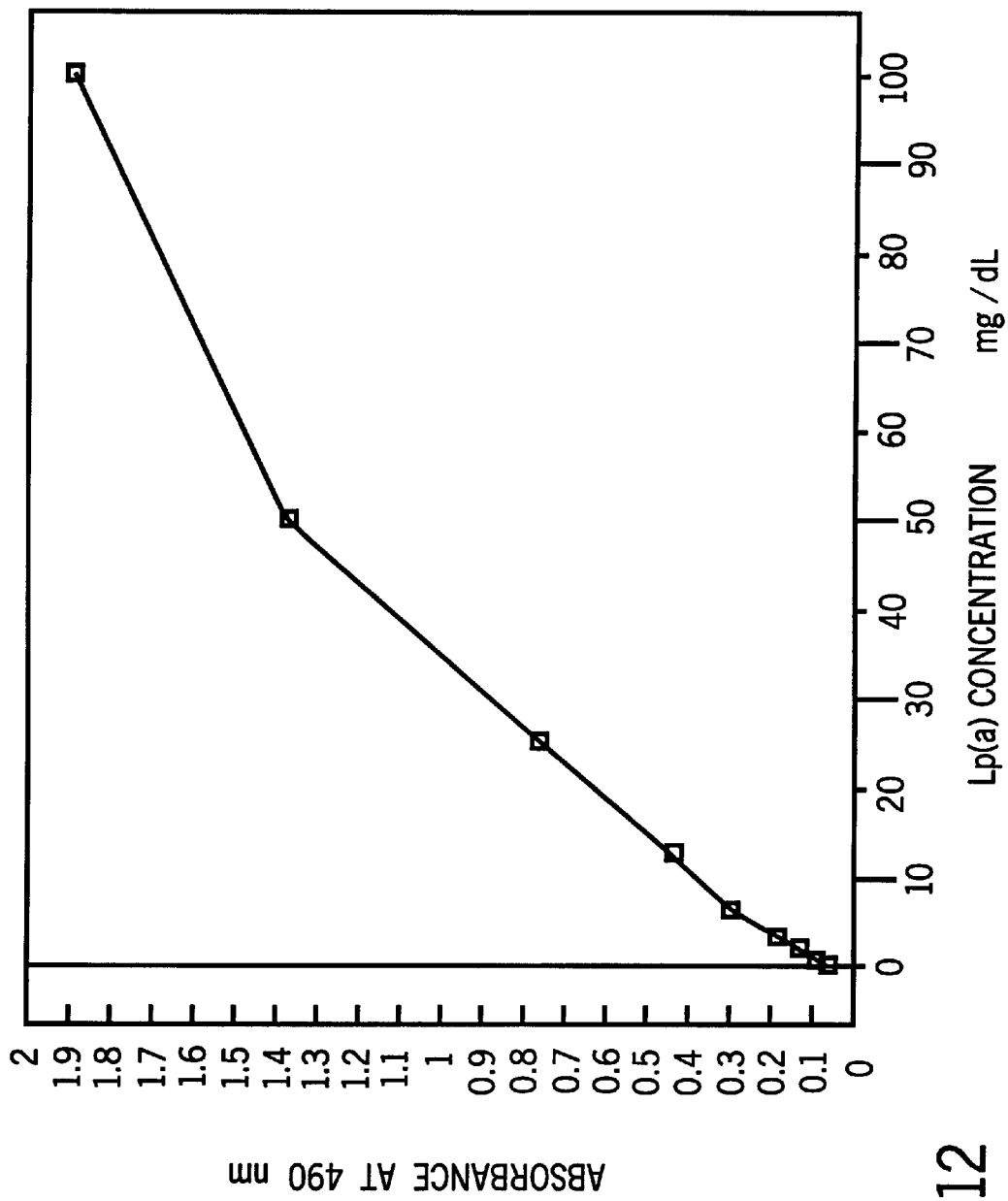
FIG. 12 shows a calibration curve of Lp(a) concentration in mg/dL versus absorbance at 490 nm using anti-kringle 4 Mab 4D2 as the capture antibody and HRPO-labeled anti-kringle 5 Mab for detection as described in Example 6.

Lp(a) Immunoassay with Anti-Kringle 4 Mab as Capture and HRPO-Labeled Anti-Kringle 5 Mab for Detection a. Anti-kringle 4 Coated Plates:

The kringle 4 specific Mab 4D2 previously described was diluted in 20 mM PBS, pH 7.4, to a final concentration of 2.5 mg/mL. One-hundred microliters of the solution were added to each well of Maxisorb Nunc Immuno plates and processed as described in Example 4a above.

b. Lp(a) Standard Curves: Lp(a) standards were prepared as described in Example 3 above. Calibrators having 0,0.0195, 0.039, 0.078, 0.156, 0.312, 0.624, 1.248 and 2.5 mg/mL were prepared by serial dilution of the 2.5 mg/mL solution made from a Lp(a) standard in 3% (v/v) FBS in 20 mM PBS at pH 7.4. One-hundred microliters of Lp(a) standards (in duplicate) were incubated in the anti-kringle 4 coated plates described above at 37° C. for one hour. After washing the plates five times with PBS-Tween, 100 mL of anti-kringle 5 Mab-HRPO conjugate (prepared as described in Section 3c above) at 0.25 mg/mL in 3% FBS in PBS was added to each well and incubated at 37° C. for one hour. The remainder of the procedure was exactly the same as described in Example 4c except that the color development was stopped with 1 N sulfuric acid at 10 minutes. The Lp(a) concentrations were multiplied by 100 to generate the standard curves because the plasma samples would be diluted 100 fold prior to performing the assay. A plot of Lp(a) concentration versus absorbance was prepared from the resulting data. FIG. 12 is illustrative of such a plot.

c. Lp(a) Immunoassay:

Plasma samples were diluted 100-fold with 3% w/v FBS in 20 mM PBS, at pH 7.4. One-hundred microliters of the diluted samples were added to each well of the kringle 4 coated plates and the plates were incubated at 37° C. for one hour. After washing the plates five times with PBS-Tween, 100 mL of anti-kringle 5 Mab HRPO conjugate (2 mg/mL in 3% w/v FBS in 20 mM PBS at pH 7.4) were added to each well. The plates were incubated at 37° C. for one hour. The remainder of the procedure was as described in Example 4c above except the color development with the substrate was for 10 minutes. The calibrators and the plasma samples were assayed on the same plate to minimize the effect of variations in the reagents, materials or conditions.

Figure 13A:
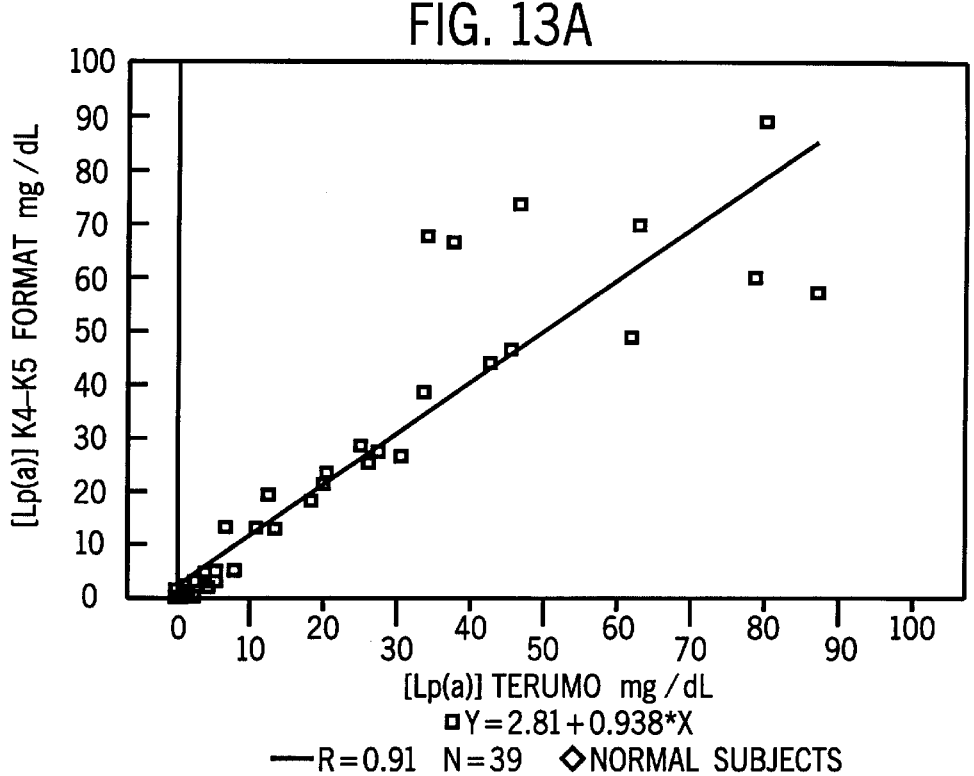
FIGS. 13A and 13B show correlation curves for Lp(a) assays using anti-kringle 4 Mab 4D2 as the capture antibody and HRPO-labeled anti-kringle Mab 1-892-230 for detection (y-axis) vs. the Terumo ELISA (x-axis).
Figure 13B:
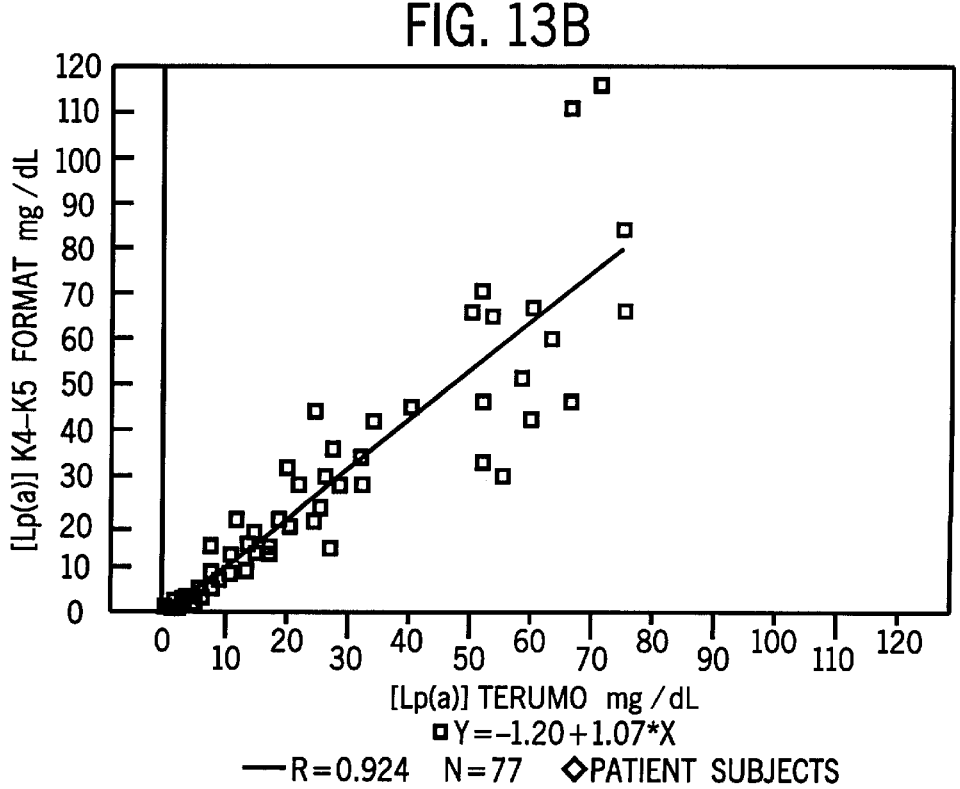

The Lp(a) concentrations of the samples are shown in Table 2 and the correlations between the Lp(a) concentrations measured by the TERUMO ELISA method and the present format are shown in FIGS. 13A and 13B. The correlation between the methods in normal subjects showed more scattering than the two other formats described in Examples 4 and 5. The correlation between the two methods in normal subjects (FIG. 13A) had a correlation coefficient (r)=0.91; intercept=2.81; slope=0.938. The correlation between the two methods in patients is reasonable below an Lp(a) concentration of 50 mg/dL (FIG. 13B); the correlations were r=0.924; intercept=−1.20; slope=1.07. The results with the present format indicate that the binding of labeled anti-kringle 5 Mab to the Lp(a) captured on the immobilized anti-kringle 4 Mab is comparatively weak. The results can possibly be improved by increasing the concentration of the labeled conjugate and/or incubation time.

EXAMPLE 7

Figure 14:
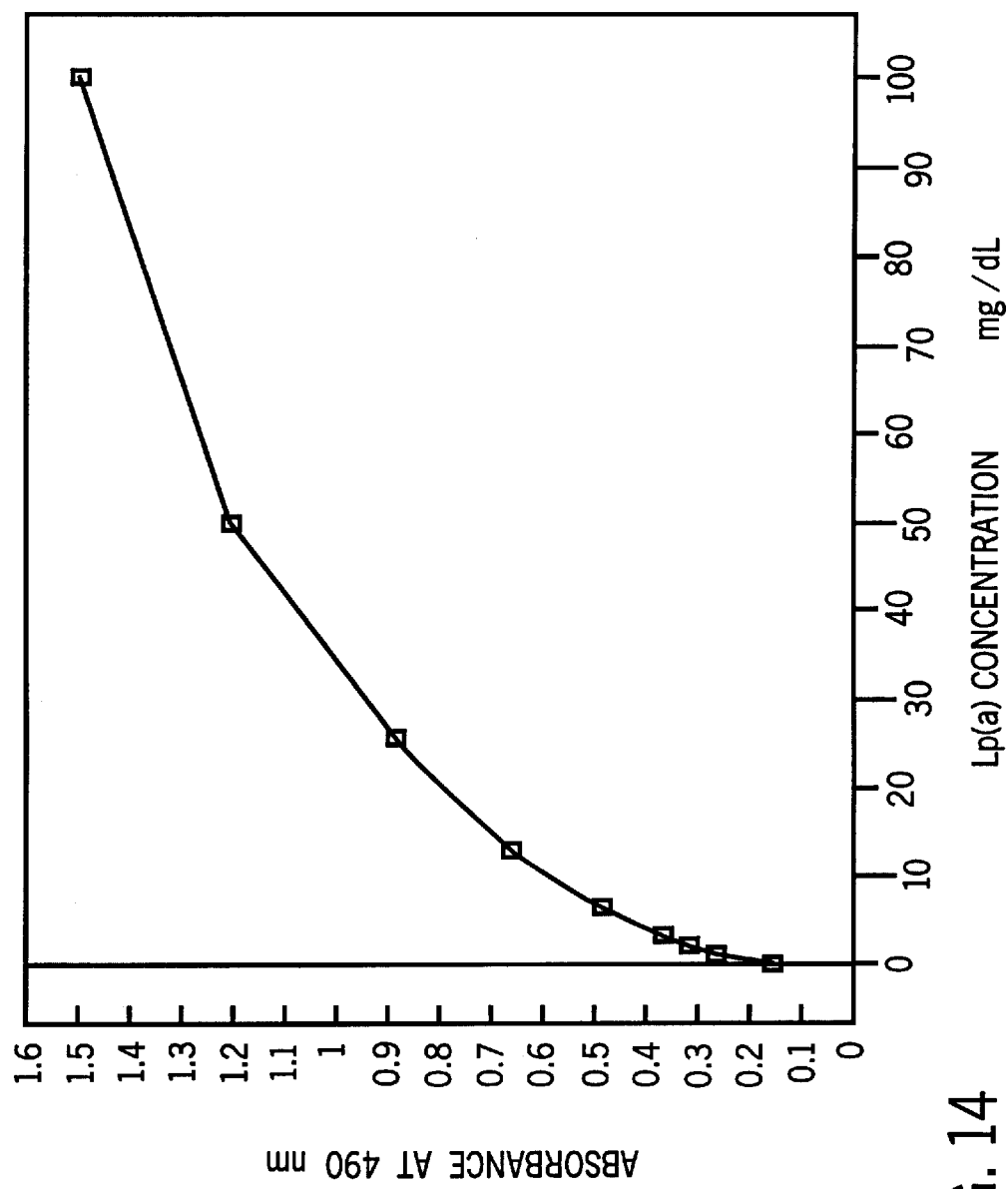
FIG. 14 shows a calibration curve of Lp(a) concentration in mg/dL versus absorbance at 490 nm using anti-apo(a) Pab as the capture antibody and HRPO-labeled anti-kringle 5 Mab for detection as described in Example 7.
Figure 15A:
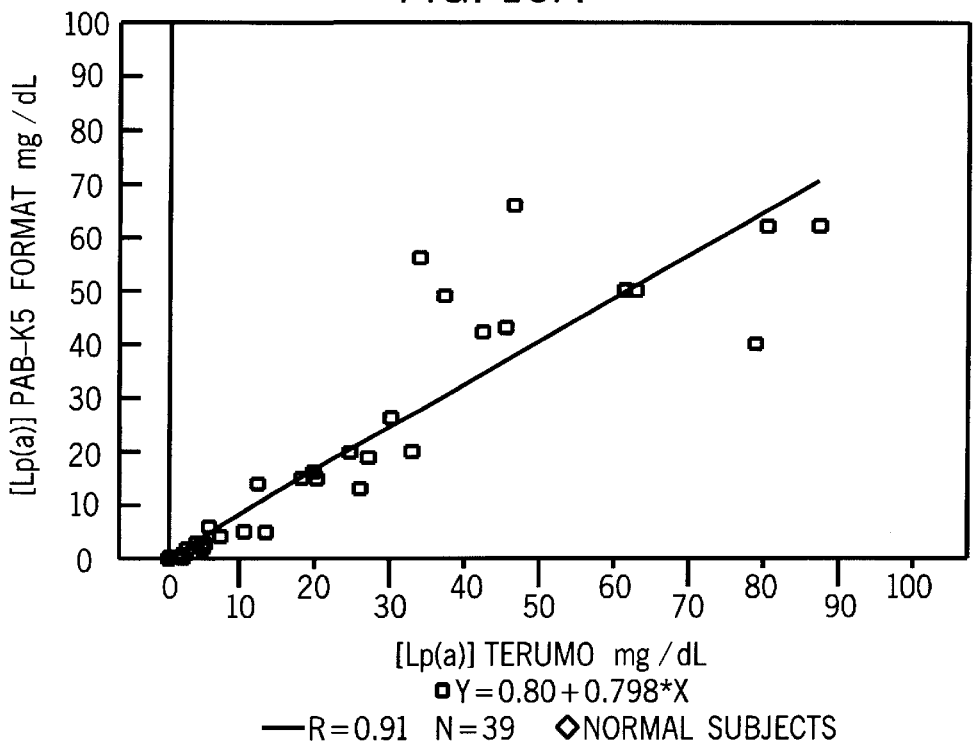
FIG. 15A and 15B show correlation curves for Lp(a) assays using sheep polyclonal anti-apo(a) as the capture antibody and HRPO-labeled anti-kringle Mab 1-892-230 for detection vs. the Terumo ELISA.
Figure 15B:
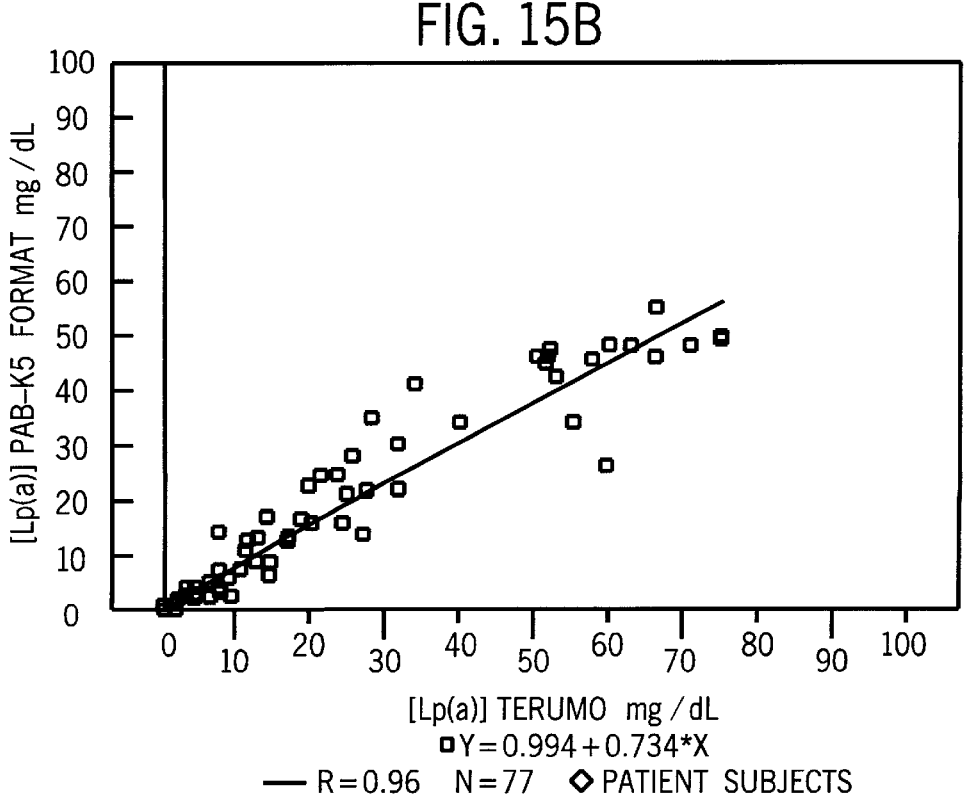

Lp(a) Immunoassay with Anti-APO(A) as Capture and HRPO-Labeled Anti-Kringle 5 Mab for Detection a. Anti-Apo(a) Coated Plates:

The sheep anti-apo(a) polyclonal antibody previously described was diluted in 20 mM PBS, pH 7.4, to a final concentration of 2.5 mg/mL. One-hundred microliters of the solution were added to each well of Maxisorb Nunc Immunoplates and processed as described in Example 4a above.

b. Standard Curves and Lp(a) Immunoassay: The generation of the Lp(a) standard curves and the Lp(a) immunoassay were performed as described in Examples 6a and 6b. The standard curve with this format is illustrated in FIG. 14. The correlations between the Lp(a) concentrations as measured by the TERUMO ELISA method and the present format in normal subjects and in patients are shown in FIGS. 15A and 15B, respectively. The correlations were: normal subjects r=0.91; intercept=0.80; slope=0.798; patients r=0.96; intercept=0.994; slope=0.734. The results indicate a similar situation to that seen in Example 6. It may be possible to improve the results by increasing the concentration of the labeled anti-kringle 5 conjugate, altering the concentration of the capture anti-apo(a) polyclonal antibody on the solid phase and/or the incubation time.

EXAMPLE 8

Figure 16:
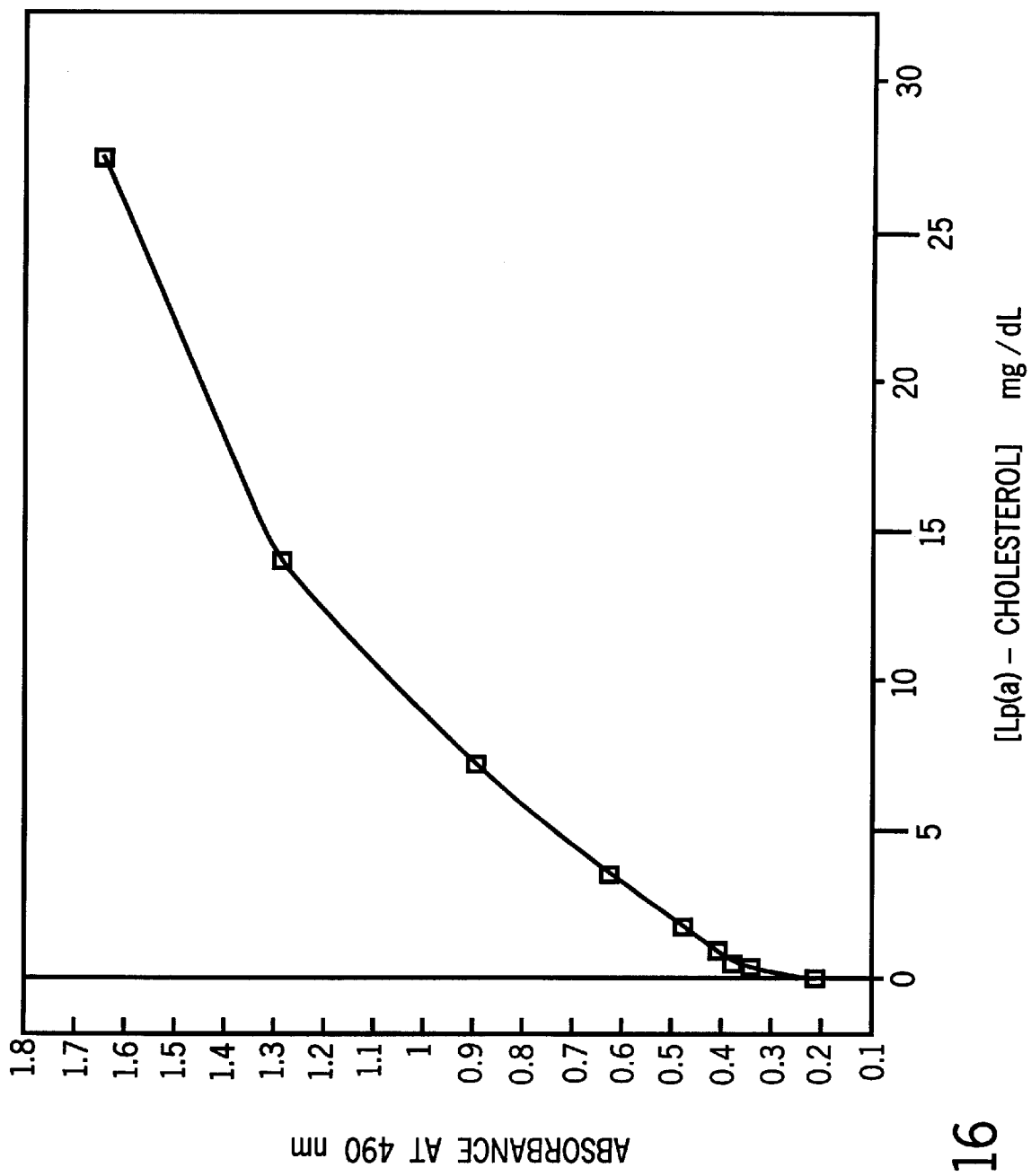
FIG. 16 shows a calibration curve of Lp(a)-cholesterol concentration in mg/dL versus absorbance at 490 nm using anti-kringle 5 Mab as the capture antibody and HRPO-labeled digitonin for detection as described in Example 8.

Lp(a)-Cholesterol Assay with Anti-Kringle 5 Mab
a. Anti-kringle 5 Coated Plates:

The kringle 5 specific Mab 1-892-230 was diluted in 20 mM PBS, pH 7.4 to a final concentration of 5 mg/mL. One-hundred microliters of the solution were added to each well of Maxisorb Nunc Immuno plates and incubated at room temperature with gentle shaking for two hours. The plates were washed five times with PBS-Tween and then blocked with 200 mL/well of 5% (v/v) BSA in 20 mM PBS by incubation at 37° C. for one hour. The plates were stored at 4° C. with plastic sealers. Before use, the plates were washed five times with PBS-Tween.

b. Lp(a)-Cholesterol Standard Curves: Lp(a)-cholesterol standards were prepared from Lp(a) standard solutions as described in Example 3. Calibrators having Lp(a)-cholesterol concentrations of 0, 0.0213, 0.0426, 0.0852, 0.170, 0.341, 0.682, 1.364 and 2.73 mg/mL were prepared by serial dilution of the 2.73 mg/mL solution made from a Lp(a) standard in 1% (w/v) alkali-treated casein in 20 mM PBS, pH 7.4. One-hundred microliters of Lp(A)-cholesterol standards (in duplicate) were incubated in the anti-kringle 5 Mab coated plates prepared above, at 37° C. for one hour. After washing the plates five times with PBS Tween, 100 mL of HRPO-digitonin conjugate (prepared as described in Section 3b above) at 1 mg/mL in 1% alkali-treated casein in 20 mM PBS, pH 7.4, was added to each well and incubated at 37° C. for 1 hour. The plates were then processed as described in Example 4c. The concentrations of Lp(a)-cholesterol were multiplied by 100 to generate the calibration curve because the plasma samples would be diluted 100-fold prior to performing the assay. A plot of Lp(a)-cholesterol concentration versus absorbance was prepared from the resulting data. FIG. 16 is illustrative of such a plot. Generally the calibrators and the plasma samples were assayed on the same plate to minimize the effect of variations in the reagents, materials or conditions. The number and concentration of calibrators used can be readily altered depending on the desired accuracy of the results.

5 c. Lp(a)-Cholesterol Immunoassay: Plasma samples were diluted 100-fold with 1% w/v alkali-treated casein in 20 mM PBS, pH 7.4. One-hundred microliters of the diluted samples were added to each well of the kringle 5 Mab coated plates, and the plates were incubated at 37° C. for one hour. After washing the plates five times with PBS-Tween, 100 mL of digitonin-HRPO conjugate (1 mg/mL in 1% w/v alkali-treated casein in 20 mM PBS, pH 7.4) were added to each well and incubated at 37° C. for one hour. The remainder of the procedure is as described in Example 4c.

Figure 17:
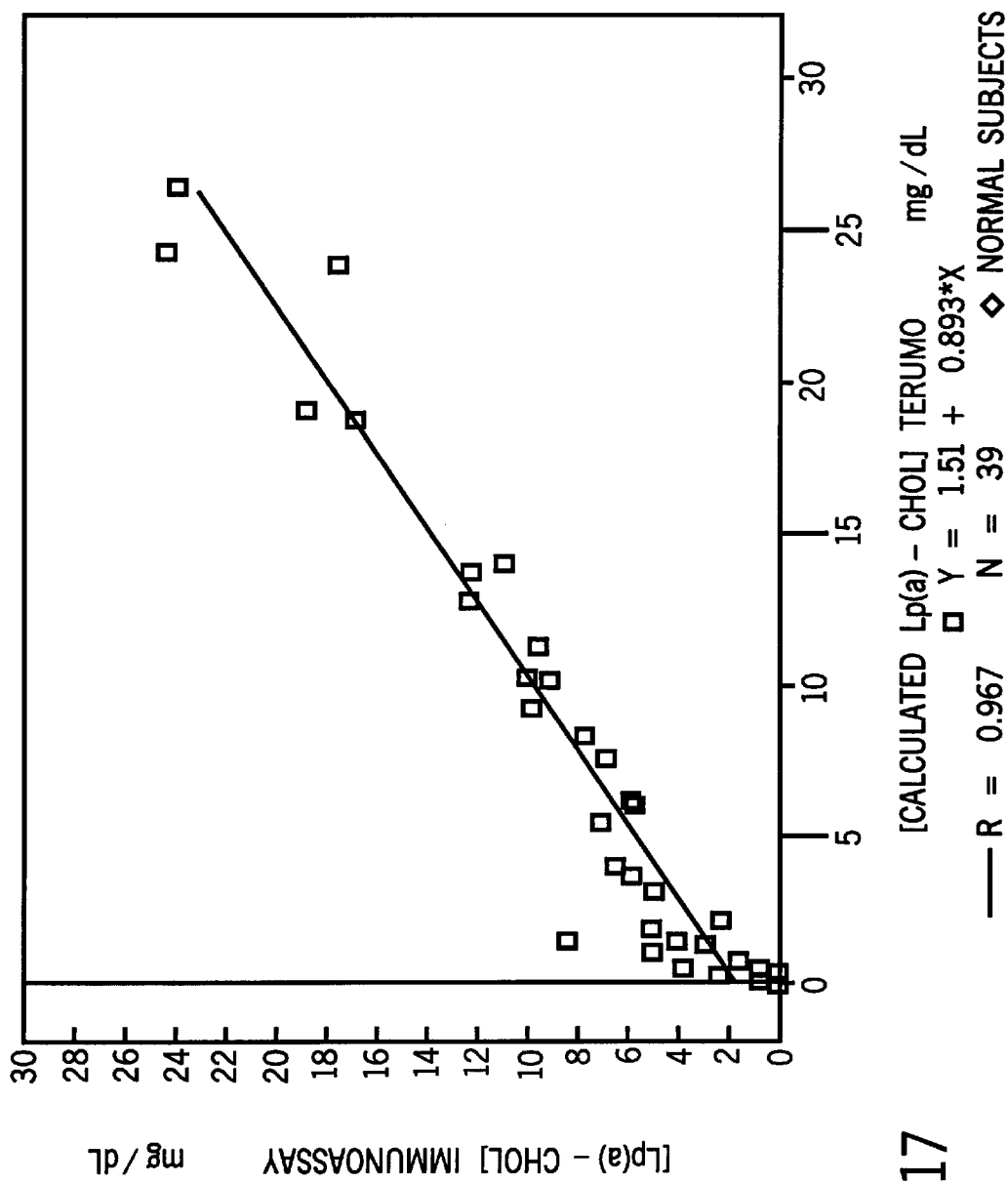
FIG. 17 shows a correlation curve for Lp(a)-cholesterol assays using anti-kringle 5 Mab 1-892-230 as the capture antibody and HRPO-labeled digitonin for detection with calculated Lp(a)-cholesterol levels obtained using the TERUMO ELISA as described in Example 8.

The Lp(a)-cholesterol concentrations of the samples derived from the TERUMO ELISA method were calculated by multiplying the Lp(a) concentration by 0.3. The results of Lp(a)-cholesterol concentrations using the immunoassay method above are shown in Table 3. FIG. 17 shows the correlation between the calculated Lp(a)-cholesterol values obtained from the TERUMO ELISA Lp(a) concentrations and the direct immunoassay method of this invention. The correlations between the methods with normal subjects are: $r=0.967$; intercept$=1.51$; slope$=0.8\ 93$.

The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

TABLE 1

LIPID PROFILES OF PLASMA SAMPLES

| Sample No. | Sample ID | Total-C mg/dL | HDL-C mg/dL | Trig mg/dL | LDL-FE mg/dL | LDL-UC mg/dL | Lp(a) mg/dL |
|---|---|---|---|---|---|---|---|
| 1 | CP | 220 | 44 | 201 | 136 | 144 | 2.5 |
| 2 | SF | 154 | 39 | 43 | 106 | 114 | 0.3 |
| 3 | CF | 227 | 38 | 80 | 161 | 150 | 61.6 |
| 4 | NS | 177 | 38 | 104 | 118 | 119 | 6.2 |
| 5 | W | 244 | 37 | 108 | 185 | 172 | 78.8 |
| 6 | RB | 173 | 37 | 94 | 117 | 119 | 44.9 |
| 7 | LL | 172 | 78 | 51 | 84 | 91 | 4.4 |
| 8 | MP | 162 | 46 | 71 | 101 | 99 | 33.5 |
| 9 | AJ | 186 | 43 | 178 | 108 | 124 | 4.1 |
| 10 | PB | 163 | 56 | 51 | 96 | 91 | 46 |
| 11 | AY | 275 | 50 | 114 | 202 | 174 | 24.5 |
| 12 | GO | 282 | 43 | 180 | 203 | 196 | 2 |
| 13 | LA | 199 | 65 | 249 | 84 | 102 | 17.9 |
| 14 | MM | 210 | 57 | 115 | 131 | 123 | 37 |
| 15 | RN | 217 | 41 | 127 | 150 | 156 | 27 |
| 16 | BC | 222 | 64 | 77 | 142 | 134 | 10.3 |
| 17 | RC | 181 | 52 | 60 | 117 | 116 | 4.8 |
| 18 | OL | 148 | 52 | 74 | 81 | 76 | 13 |
| 19 | JS | 162 | 44 | 71 | 104 | 98 | 1.4 |
| 20 | MS | 208 | 38 | 131 | 143 | 148 | 4 |
| 21 | LT | 182 | 70 | 37 | 104 | 104 | 1.5 |
| 22 | JC | 160 | 55 | 104 | 84 | 84 | 87 |
| 23 | HB | 155 | 34 | 68 | 107 | 107 | 1 |
| 24 | TS | 130 | 33 | 73 | 83 | 88 | 0.97 |
| 25 | RR | 214 | 42 | 52 | 162 | 164 | 0.2 |
| 26 | ML | 236 | 61 | 108 | 154 | 145 | 4.84 |
| 27 | EB | 163 | 65 | 44 | 89 | 89 | 1.7 |
| 28 | JR | 142 | 41 | 130 | 75 | 85 | 30 |
| 29 | DK | 166 | 35 | 82 | 115 | 101 | 2 |
| 30 | GC | 241 | 61 | 74 | 165 | 165 | 80 |
| 31 | LR | 135 | 43 | 77 | 77 | 68 | 7.4 |
| 32 | SD | 227 | 32 | 365 | 122 | 137 | 1.2 |
| 33 | JM08810 | n/a | n/a | n/a | n/a | n/a | 12 |
| 34 | JM08806 | n/a | n/a | n/a | n/a | n/a | 20 |
| 35 | JM08657 | 211 | 40 | 99 | 150 | 147 | 33 |
| 36 | JM08632 | 178 | 35 | 70 | 87 | n/a | 62.6 |
| 37 | WO | 197 | 55 | 44 | 133 | 123 | 42 |
| 38 | SK | 230 | 47 | 109 | 150 | 161 | 25.8 |

TABLE 1-continued

UPID PROFILES OF PLASMA SAMPLES

| Sample No. | Sample ID | Total-C mg/dL | HDL-C mg/dL | Trig mg/dL | LDL-FE mg/dL | LDL-UC mg/dL | Lp(a) mg/dL |
|---|---|---|---|---|---|---|---|
| 39 | BP | 215 | 63 | 68 | 138 | 148 | 19.5 |
| 40 | ES639 | 160 | 32 | 172 | 94 | 93 | 9.5 |
| 41 | ES629 | 294 | 70 | 134 | 197 | 205 | 14.4 |
| 42 | ES211 | 172 | 68 | 73 | 89 | 20? | 0.3 |
| 43 | ES600 | 289 | 36 | 299 | 193 | 202 | 2.3 |
| 44 | ES337 | 192 | 41 | 118 | 127 | 129 | 1.8 |
| 45 | ES161 | 176 | 54 | 68 | 108 | 111 | 22 |
| 46 | ES147 | 243 | 43 | 182 | 164 | 176 | 63 |
| 47 | BS596 | 256 | 43 | 179 | 177 | 167 | 34 |
| 48 | ES284 | 198 | 33 | 184 | 128 | 113 | 60 |
| 49 | ES652 | 157 | 66 | 156 | 60 | 71 | 2 |
| 50 | ES651 | 228 | 70 | 91 | 140 | 144 | 75 |
| 51 | ES290 | 196 | 42 | 161 | 122 | 116 | 4.4 |
| 52 | ES15 | 255 | 39 | 206 | 175 | 171 | 20 |
| 53 | ES13 | 173 | 35 | 93 | 119 | 115 | 14.7 |
| 54 | ES572 | 345 | 50 | 313 | 232 | 234 | 28.3 |
| 55 | ES129 | 221 | 59 | 146 | 133 | 132 | 75 |
| 56 | ES146 | 199 | 48 | 93 | 132 | 139 | 32 |
| 57 | ES453 | 298 | 74 | 116 | 201 | 204 | 2.5 |
| 58 | ES593 | 174 | 47 | 126 | 102 | 105 | 13.6 |
| 59 | ES571 | 209 | 42 | 193 | 128 | 128 | 4.4 |
| 60 | ES151 | 238 | 40 | 214 | 155 | 163 | 20 |
| 61 | ES2 | 172 | 45 | 120 | 103 | 105 | 10.5 |
| 62 | ES17 | 259 | 67 | 101 | 172 | 181 | 11 |
| 63 | ES10 | 204 | 33 | 148 | 141 | 143 | 7.8 |
| 64 | ES9 | 165 | 35 | 83 | 113 | 120 | 1 |
| 65 | ES19 | 194 | 48 | 131 | 120 | 125 | 53 |
| 66 | ES12 | 225 | 35 | 151 | 160 | 167 | 50 |
| 67 | ES193 | 190 | 41 | 87 | 132 | 139 | 26 |
| 68 | ES153 | 218 | 40 | 178 | 142 | 148 | 78 |
| 69 | ES7 | 365 | 44 | 411 | — | 225 | 27.5 |
| 70 | ES651 | 228 | 70 | 91 | 140 | 144 | 75 |
| 71 | ES11 | 249 | 41 | 185 | 171 | 167 | 3.6 |
| 72 | ES8 | 336 | 62 | 151 | 244 | 251 | 9.2 |
| 73 | ES4 | 267 | 30 | 331 | 171 | 172 | 4.4 |
| 74 | ES327 | 200 | 52 | 170 | 114 | 104 | 52 |
| 75 | E3 | 228 | 52 | 120 | 152 | 161 | 59.6 |
| 76 | ES582 | 237 | 48 | 90 | 171 | 169 | 30 |
| 77 | ES14 | 246 | 55 | 101 | 171 | 167 | 7.6 |
| 78 | ES127 | 309 | 39 | 68 | 256 | 266 | 8.9 |
| 79 | D7 | 220 | 43 | 145 | 149 | | 1.9 |
| 86 | D7944 | 232 | 44 | 335 | 122 | | 24.4 |
| 81 | D746 | 348 | 40 | 350 | 119 | | 06.2 |
| 82 | D1782 | 170 | 30 | 159 | 108 | | 1.4 |
| 83 | D2237 | 205 | 44 | 111 | 139 | | 5 |
| 84 | D1767 | 204 | 51 | 136 | 126 | | 71 |
| 85 | D2713 | 183 | 59 | 91 | 106 | | 13.3 |
| 86 | D2892 | 312 | 46 | 481 | 170 | | 2.6 |
| 87 | D1784 | 197 | 34 | 193 | 124 | | 4.6 |
| 88 | D2714 | 240 | 38 | 278 | 147 | | 66.2 |
| 89 | D2165 | 250 | 36 | 541 | 106 | | 0.6 |
| 90 | D2429 | 169 | 32 | 107 | 116 | | 3.1 |
| 91 | D2166 | 211 | 56 | 319 | 91 | | 8.1 |
| 92 | D2283 | 303 | 18 | 394 | 206 | | 4.3 |
| 93 | D2242 | 200 | 52 | 150 | 118 | | 8 |
| 94 | D1968 | 249 | 47 | 175 | 167 | | 0.6 |
| 95 | D1765 | 316 | 38 | 294 | 219 | | 66.2 |
| 96 | D2465 | 164 | 28 | 250 | 85 | | 11.8 |
| 97 | D2743 | 164 | 41 | 108 | 102 | | 26.9 |
| 98 | D2688 | 197 | 35 | 191 | 124 | | 32 |
| 99 | D1983 | 136 | 41 | 229 | 49 | | 25.4 |
| 100 | D1494 | 167 | 28 | 240 | 91 | | 0.9 |
| 101 | D1619 | 232 | 61 | 69 | 157 | | 17.2 |
| 102 | D2298 | 129 | 37 | 109 | 70 | | 6.3 |
| 103 | D2294 | 215 | 48 | 281 | 112 | | 14.7 |
| 104 | D1766 | 255 | 38 | 200 | 177 | | 10.9 |
| 105 | D2426 | 185 | 46 | 215 | 96 | | 1.9 |
| 106 | D1517 | 195 | 40 | 443 | 66 | | 2.93 |
| 107 | D2310 | 136 | 37 | 134 | 72 | | 0.4 |
| 108 | D7986 | 213 | 46 | 245 | 118 | | 51.8 |
| 109 | D25 | 193 | 36 | 121 | 133 | 131 | 51.3 |
| 110 | D26 | 214 | 48 | 75 | 151 | 161 | 1.7 |
| 111 | D27 | 199 | 40 | 142 | 13.1 | | 18.8 |
| 112 | D28 | 106 | 46 | 60 | 48 | 57 | 7.87 |

TABLE 1-continued

LIPID PROFILES OF PLASMA SAMPLES

| Sample No. | Sample ID | Total-C mg/dL | HDL-C mg/dL | Trig mg/dL | LDL-FE mg/dL | LDL-UC mg/dL | Lp(a) mg/dL |
|---|---|---|---|---|---|---|---|
| 113 | D29 | 166 | 38 | 30 | 98 | 107 | 24.3 |
| 114 | D30 | 227 | 55 | 127 | 147 | 174 | N/D |
| 115 | D34 | 164 | 72 | 58 | 81 | 77 | N/D |
| 116 | D35 | 221 | 74 | 101 | 127 | 11.8 | N/D |

C = Cholesterol; FE = Friedewald calculated; UC = Ultracentrifuged (B-Quantitation)
*Samples 1 to 39 are normal subjects, from 40 to 78 are patients who are on lipid lowering drugs and from 79 to 116 are diabetic patients

TABLE 2

Lp(a) CONCENTRATION BY IMMUNOASSAY

| Sample No. | Sample ID* | Lp(a) mg/dL Ref Meth** | Lp(a) mg/dL Format 1 | Lp(a) mg/dL Format 2 | Lp(a) mg/dL Format 3 | Lp(a) mg/dL Format 4 |
|---|---|---|---|---|---|---|
| 1 | CP | 2.5 | 3 | 2.6 | 4 | 1 |
| 2 | SF | 0.3 | 0.2 | 0.2 | 1 | 0.3 |
| 3 | CF | 61.6 | 58 | 70 | 48 | 50 |
| 4 | NS | 6.2 | 8 | 9 | 13 | 6 |
| 5 | DW | 78.8 | 71 | 70 | 59 | 40 |
| 6 | RB | 44.9 | 33.5 | 35 | 46 | 43 |
| 7 | LL | 4.4 | 4 | 5.8 | 3.5 | 3 |
| 8 | MP | 33.5 | 35 | 60 | 67 | 56 |
| 9 | AJ | 4.1 | 3.5 | 4.9 | 2 | 2 |
| 10 | PB | 46 | 48 | 59 | 73 | 66 |
| 11 | AY | 24.5 | 33 | 30 | 28 | 20 |
| 12 | GO | 2 | 1.5 | 1.5 | 1.4 | 0.6 |
| 13 | LA | 17.9 | 31 | 31 | 18 | 15 |
| 14 | MM | 37 | 41 | 47 | 66 | 49 |
| 15 | RN | 27 | 25 | 41 | 27 | 19 |
| 16 | BC | 10.3 | 14 | 12.6 | 12.8 | 5 |
| 17 | RC | 4.8 | 6.5 | 5.8 | 4.7 | 2.2 |
| 18 | OL | 13 | 13.8 | 12.6 | 13 | 5 |
| 19 | JS | 1.4 | 1 | 1 | 1.2 | 0.5 |
| 20 | MS | 4 | 5.3 | 6 | 3.2 | 3 |
| 21 | LT | 1.5 | 0.5 | 0.5 | 0.2 | 0.3 |
| 22 | JC | 87 | 77 | 70 | 56 | 62 |
| 23 | HB | 1 | 1 | 1 | 0.5 | 0.4 |
| 24 | TS | 0.97 | 0.6 | 0.5 | 0.8 | 0.3 |
| 25 | RR | 0.2 | 0.1 | 0.1 | 0.1 | 0.1 |
| 26 | ML | 4.84 | 6 | 6.5 | 3 | 2.4 |
| 27 | EB | 1.7 | 1 | 1 | 0.5 | 0.4 |
| 28 | JR | 30 | 33 | 32 | 26 | 26 |
| 29 | DK | 2 | 2 | 2 | 1 | 0.5 |
| 30 | GC | 80 | 67 | 89 | 88 | 62 |
| 31 | LR | 7.4 | 9.8 | 10.7 | 5 | 4 |
| 32 | SD | 1.2 | 0.5 | 0.6 | 2 | 0.2 |
| 33 | JMO8810 | 12 | 15 | 22 | 19 | 14 |
| 34 | JM08806 | 20 | 17 | 24 | 23 | 15 |
| 35 | JM08657 | 33 | 24 | 24 | 38 | 20 |
| 36 | JM08632 | 62.6 | 62 | 76 | 69 | 50 |
| 37 | WO | 42 | 43 | 39.5 | 43.5 | 42 |
| 38 | SK | 25.8 | 28 | 38 | 25 | 13 |
| 39 | BP | 19.5 | 18 | 24 | 21 | 16 |
| 40 | ES639 | 9.5 | 8.2 | 6.7 | 8 | 2.5 |
| 41 | ES629 | 14.4 | 16.5 | 22 | 15 | 8.7 |
| 42 | ES211 | 0.3 | 0.5 | 0.8 | 0.8 | 0.8 |
| 43 | ES600 | 2.3 | 3.6 | 6.1 | 2.3 | 2 |
| 44 | ES337 | 1.8 | 1 | 1.2 | 1.5 | 0.5 |
| 45 | ES161 | 22 | 24.5 | 36 | 27 | 24 |
| 46 | ES147 | 63 | 83 | 88 | 59 | 48 |
| 47 | ES596 | 34 | 46 | 50 | 41 | 41 |
| 48 | ES284 | 60 | 62.3 | 65 | 66 | 48 |
| 49 | ES652 | 2 | 1.4 | 1.6 | 2.1 | 1 |
| 50 | ES651 | 75 | 81 | 83 | 83 | 49 |
| 51 | ES290 | 4.4 | 4.7 | 7 | 3.1 | 3.5 |
| 52 | ES15 | 20 | 18.5 | 25.8 | 18.5 | 16 |
| 53 | ES13 | 14.7 | 18.4 | 24.4 | 17.1 | 17 |
| 54 | ES572 | 28.3 | 35 | 44 | 27.4 | 35 |
| 55 | ES129 | 75 | 65 | 64 | 65 | 49.5 |

TABLE 2-continued

Lp(a) CONCENTRATION BY IMMUNOASSAY

| Sample No. | Sample ID* | Lp(a) mg/dL Ref Meth** | Lp(a) mg/dL Format 1 | Lp(a) mg/dL Format 2 | Lp(a) mg/dL Format 3 | Lp(a) mg/dL Format 4 |
|---|---|---|---|---|---|---|
| 56 | ES146 | 32 | 40 | 50 | 27 | 22 |
| 57 | ES453 | 2.5 | 4;5 | 6.4 | 1.7 | 1.6 |
| 58 | ES593 | 13.6 | 16.5 | 20.7 | 15 | 13 |
| 59 | ES571 | 4.4 | 4.1 | 6.4 | 3 | 3.5 |
| 60 | ES151 | 20 | 27 | 35 | 31 | 23 |
| 61 | ES2 | 10.5 | 14 | 26 | 7.7 | 7.2 |
| 62 | ES17 | 11 | 12 | 12 | 12 | 11 |
| 63 | ES10 | 7.8 | 6 | 5.4 | 8.5 | 4.2 |
| 64 | ES9 | 1 | 0.5 | 0.6 | 1 | 0.5 |
| 65 | ES19 | 53 | 69.2 | 82 | 64 | 42 |
| 66 | ES12 | 50 | 75 | 75 | 65 | 46 |
| 67 | ES193 | 26 | 46 | 44 | 29 | 28 |
| 68 | ES153 | 40 | 35 | 38 | 44 | 34 |
| 69 | ES7 | 27.5 | 24.34 | 34.8 | 35 | 22 |
| 70 | ES651 | 75 | 81 | 92 | 83 | 49 |
| 71 | ES11 | 3.6 | 6 | 2.1 | 4 | 4.2 |
| 72 | ES8 | 9.2 | 14 | 29.6 | 7 | 6 |
| 73 | ES4 | 4.4 | 3 | 5 | 2.4 | 2.2 |
| 74 | ES327 | 52 | 85 | 79 | 45 | 47 |
| 75 | ES3 | 59.6 | 55.4 | 64.5 | 41 | 26 |
| 76 | ES582 | 17 | 21.5 | 22 | 14 | 12.5 |
| 77 | ES14 | 7.6 | 14 | 10 | 14 | 14 |
| 78 | ES127 | 8.9 | 11 | 12.5 | 6.5 | 6 |
| 79 | D7 | 1.9 | 1.7 | 1.9 | 1.3 | 1.1 |
| 80 | D7944 | 24.4 | 36.1 | 38.7 | 43.5 | 23.7 |
| 81 | D746 | 6.2 | 7.1 | 6 | 2.8 | 3 |
| 82 | D1782 | 1.4 | 1.3 | 1.5 | 0.4 | 1 |
| 83 | D2237 | 5 | 5.4 | 5.4 | 2 | 2.9 |
| 84 | D1767 | 71 | 115 | 100 | 115 | 48 |
| 85 | D2713 | 13.3 | 22.3 | 19.7 | 8.6 | 9.1 |
| 86 | D2892 | 2.6 | 3.7 | 3.6 | 1.4 | 1.6 |
| 87 | D1784 | 4.6 | 5.2 | 4.7 | 1.5 | 2.1 |
| 88 | D2714 | 66.2 | 104 | 100 | 45 | 46 |
| 89 | D2165 | 0.6 | 0.7 | 0.7 | 0.2 | 0.3 |
| 90 | D2429 | 3.1 | 4.3 | 4.8 | 1.6 | 2.7 |
| 91 | D2166 | 8.1 | 12.3 | 12.6 | 6.7 | 7.4 |
| 92 | D2283 | 4.3 | 6.1 | 7.2 | 3.1 | 4 |
| 93 | D2242 | 8 | 8.9 | 8 | 5.7 | 3.1 |
| 94 | D1968 | 0.6 | 0.2 | 0.2 | 0.2 | 0.2 |
| 95 | D1765 | 66.2 | 107 | 110 | 110 | 55.2 |
| 96 | D2465 | 11.8 | 19.3 | 20.7 | 20 | 12.8 |
| 97 | D2743 | 26.9 | 36 | 29 | 13.5 | 13.8 |
| 98 | D2688 | 32 | 53 | 52 | 33 | 30 |
| 99 | D1983 | 25.4 | 38 | 42 | 22.4 | 21 |
| 100 | D1494 | 0.9 | 0.5 | 0.7 | 0.2 | 0.2 |
| 101 | D1619 | 17.2 | 29.6 | 28.6 | 12 | 13.3 |
| 102 | D2298 | 6.3 | 9.5 | 11.5 | 5 | 5.3 |
| 103 | D2294 | 14.7 | 18 | 16.4 | 12.8 | 6.3 |
| 104 | D1766 | 10.9 | 16.4 | 18 | 8.1 | 8.9 |
| 105 | D2426 | 1.9 | 1.1 | 1.3 | 0.6 | 0.5 |
| 106 | D1517 | 2.93 | 6.9 | 6.9 | 2.2 | 2.4 |
| 107 | D2310 | 0.4 | 0.2 | 0.3 | 0.1 | 0.1 |
| 108 | D7986 | 51.8 | 55 | 69.4 | 32 | 46.2 |
| 109 | D25 | 51.3 | 92.4 | 94.9 | 69.7 | 44.7 |
| 110 | D26 | 1.7 | 1 | 1.3 | 0.8 | 0.5 |
| 111 | D27 | 18.8 | 25.6 | 25.7 | 19.6 | 16.5 |
| 112 | D28 | 7.87 | 7.4 | 7.3 | 4.7 | 3.9 |
| 113 | D29 | 24.3 | 29.7 | 30 | 19.4 | 15.8 |
| 114 | D30 | 55 | 63 | 65 | 29 | 33.8 |
| 115 | D34 | 1.7 | 1 | 1.6 | 1 | 0.6 |
| 116 | D35 | 58 | 101 | 100 | 50 | 45.5 |

*Measured by TERUMO ELISA
Format 1: K5 Mab capture/K4 Mab -enzyme as a label
Format 2: K5 Mab capture/Pab -enzyme as a label
Format 3: K4 Mab capture/K5 -enzyme as a label
Format 4: Pab capture/K5 -enzyme as a label

TABLE 3

Lp(a)-CHOLESTEROL BY IMMUNOASSAY

| Sample No. | Sample ID | Lp(a) mg/dL Ref Meth** | Lp(a)-C** mg/dL | Lp(a)-C mg/dL EIA |
|---|---|---|---|---|
| 1 | CP | 2.5 | 0.8 | 1.5 |
| 2 | SF | 0.3 | 0.1 | 0.1 |
| 3 | CF | 61.6 | 18.5 | 18.0 |
| 4 | NS | 6.2 | 1.9 | 5.0 |
| 5 | DW | 78.8 | 23.6 | 19.0 |
| 6 | RB | 44.9 | 13.5 | 13.0 |
| 7 | LL | 4.4 | 1.3 | 2.9 |
| 8 | MP | 33.5 | 10.1 | 10.6 |
| 9 | AJ | 4.1 | 1.2 | 5.0 |
| 10 | PB | 46 | 13.8 | 11.6 |
| 11 | AY | 24.5 | 7.4 | 7.2 |
| 12 | GO | 2 | 0.6 | 0.7 |
| 13 | LA | 17.9 | 5.4 | 7.3 |
| 14 | MM | 37 | 11.1 | 10.1 |
| 15 | RN | 27 | 8.1 | 8.0 |
| 16 | BC | 10.3 | 3.1 | 5.0 |
| 17 | RC | 4.8 | 1.4 | 8.5 |
| 18 | OL | 13 | 3.9 | 6.6 |
| 19 | JS | 1.4 | 0.4 | 2.2 |
| 20 | MS | 4 | 1.2 | 4.9 |
| 21 | LT | 1.5 | 0.5 | 0.1 |
| 22 | JC | 87 | 26.1 | 25.6 |
| 23 | HB | 1 | 0.3 | 0.6 |
| 24 | TS | 0.97 | 0.3 | 0.6 |
| 25 | RR | 0.2 | 0.1 | 0.1 |
| 26 | ML | 4.84 | 1.5 | 4.0 |
| 27 | EB | 1.7 | 0.5 | 0.1 |
| 28 | JR | 30 | 9.0 | 10.3 |
| 29 | DK | 2 | 0.6 | 3.7 |
| 30 | GC | 80 | 24.0 | 26.0 |
| 31 | LR | 7.4 | 2.2 | 2.2 |
| 32 | SD | 1.2 | 0.4 | 0.1 |
| 33 | JMO8810 | 12 | 3.6 | 6.0 |
| 34 | JMO8806 | 20 | 6.0 | 6.0 |
| 35 | JMO8657 | 33 | 9.9 | 9.7 |
| 36 | JMO8632 | 62.6 | 18.8 | 20.0 |
| 37 | WO | 42 | 12.6 | 13.0 |
| 38 | DG | 0.8 | 0.2 | 0.7 |
| 39 | SK | 19.6 | 5.9 | 5.9 |
| 40 | ES639 | 9.5 | 2.9 | 7.6 |
| 41 | ES629 | 14.4 | 4.3 | 13.8 |
| 42 | ES211 | 0.3 | 0.3 | 2.0 |
| 43 | ES600 | 2.3 | 0.7 | 9.2 |
| 44 | ES337 | 1.8 | 0.5 | 1.3 |
| 45 | ES161 | 22 | 6.6 | 6.8 |
| 46 | ES147 | 63 | 18.9 | 12.5 |
| 47 | ES596 | 34 | 10.2 | 11.3 |
| 48 | ES284 | 60 | 18.0 | 21.3 |
| 49 | ES652 | 2 | 0.6 | 1.9 |
| 50 | ES651 | 75 | 22.5 | 17.6 |
| 51 | ES290 | 4.4 | 1.3 | 2.7 |
| 52 | ES15 | 20 | 6.0 | 10.5 |
| 53 | ES13 | 14.7 | 4.4 | 8.5 |
| 54 | ES572 | 28.3 | 8.5 | 10.3 |
| 55 | ES129 | 75 | 22.5 | 22.5 |
| 56 | ES146 | 32 | 9.6 | 17.6 |
| 57 | ES453 | 2.5 | 0.8 | 6.8 |
| 58 | ES593 | 13.6 | 4.1 | 10.1 |
| 59 | ES571 | 4.4 | 1.3 | 4.8 |
| 60 | ES151 | 20 | 6.0 | 8.0 |
| 61 | ES2 | 10.5 | 3.2 | 6.4 |
| 62 | ES17 | 11 | 3.3 | 15.1 |
| 63 | ES10 | 7.8 | 2.3 | 13.4 |
| 64 | ES9 | 1 | 0.3 | 0.5 |
| 65 | ES19 | 53 | 15.9 | 21.3 |
| 66 | ES12 | 50 | 15.0 | 21.6 |
| 67 | ES193 | 26 | 7.8 | 17.3 |
| 68 | ES153 | 40 | 12.0 | 22.8 |
| 69 | ES7 | 27.5 | 8.3 | 19.0 |
| 70 | ES651 | 75 | 22.5 | 19.5 |
| 71 | ES11 | 3.6 | 1.1 | 4.9 |
| 72 | ES8 | 9.2 | 2.8 | 18.4 |
| 73 | ES4 | 4.4 | 1.3 | 3.6 |
| 74 | ES327 | 52 | 15.6 | 24.7 |
| 75 | ES3 | 59.6 | 17.9 | 17.8 |
| 76 | ES582 | 17 | 5.1 | 11.0 |
| 77 | ES14 | 7.6 | 2.3 | 17.5 |
| 78 | ES127 | 8.9 | 2.7 | 8.0 |

What is claimed is:

1. A method for determining the amount of Lp(a) in a sample comprising the steps of:
   (a) contacting said sample and an Lp(a) specific binding agent coupled to a solid support wherein said Lp(a) specific binding agent is a monoclonal antibody or fragment thereof that binds to substantially all Lp(a) via kringle 5 of apo(a), to plasminogen at less than 1% of Lp(a) binding and to LDL, VLDL, IDL and HDL at less than 2% of Lp(a) binding, for a time and under conditions to form binding agent-Lp(a) complexes; and
   (b) determining the amount of Lp(a) bound to said binding agent-Lp(a) complexes.

2. The method of claim 1 wherein said monoclonal antibody is selected from the group consisting of Mab Nos. 1-532-266, 1-390-191, 1-458-165, 1-892-230, 1-292-189, 1-431-378, 1-746-183, and 1-546-264.

3. The method of claim 1 wherein the solid support is selected from the group consisting of nitrocellulose, latex, nylon, polystyrene, beads, particles, magnetic particles, and glass fiber.

4. The method of claim 1 further comprising the step of separating said solid support from said sample before determining the amount of Lp(a) bound to said binding agent-Lp(a) complexes.

5. The method of claim 1 further comprising contacting an indicator reagent with said sample and said Lp(a) specific binding agent prior to step (b).

6. The method of claim 5 wherein said indicator reagent is selected from the group consisting of K4 specific monoclonal antibody, K4 polyclonal antibody, K4/K5 monoclonal antibody, K4/K5 polyclonal antibody and fragments of each.

7. The method of claim 5 further comprising the step of separating said solid support from said sample before determining the amount of Lp(a) bound to said binding agent-Lp(a) complexes.

8. The method of claim 5 wherein said Lp(a) specific binding agent is selected from the group consisting of Mab Nos. 1-532-266, 1-390-191, 1-458-165, 1-892-230, 1-292-189, 1-431-378, 1-746-183, and 1-546-264.

9. A method for determining the amount of Lp(a) in a sample comprising the steps of:
   (a) contacting said sample, an indicator reagent, and a capture reagent bound to a solid support wherein said indicator reagent is a labeled monoclonal antibody or fragment thereof that binds to substantially all Lp(a) via kringle 5 of apo(a), to plasminogen at less than 1% of Lp(a) binding and to LDL, VLDL, IDL and HDL at less than 2% of Lp(a) binding, for a time and under conditions to form capture reagent-Lp(a)-indicator reagent complexes; and
   (b) determining the amount of Lp(a) bound to said binding agent-Lp(a) complexes.

10. The method of claim 9 wherein said capture reagent is selected from the group consisting of K4 specific monoclonal antibody or a fragment thereof, K4 polyclonal antibody, K4 and K5 monoclonal antibody, K4 and K5 polyclonal antibody and fragments of each.

11. The method of claim 9 further comprising the step of separating said solid support from said sample before determining the amount of Lp(a) bound to said binding agent-Lp(a) complexes.

12. The method of claim 9 wherein said indicator reagent is selected from the group consisting of Mab Nos. 1-532-266, 1-390-191, 1-458-165, 1-892-230, 1-292-189, 1-431-378, 1-746-183, and 1-546-264.

13. A method for determining the amount of Lp(a) in a sample comprising the steps of:
   (a) contacting said sample, an Lp(a) specific binding agent wherein said Lp(a) specific binding agent is conjugated to a first charged substance, and an indicator reagent wherein said indicator reagent is monoclonal antibody or fragment thereof that specifically binds to kringle 5 of apo(a) for a time and under conditions to form binding agent-Lp(a)-indicator complexes;
   (c) contacting an insoluble solid phase material which is oppositely charged with respect to said first charged substance, such that said solid phase material attracts and attaches to said first charged substance; and
   (d) determining the amount of Lp(a) bound to said binding agent-Lp(a)-indicator reagent complexes.

14. The method of claim 13 wherein said monoclonal antibody is selected from the group consisting of Mab Nos. 1-532-266, 1-390-191, 1-458-165, 1-892-230, 1-292-189, 1-431-378, 1-746-183, and 1-546-264.

15. The method of claim 13 wherein said first charged substance is an anionic or cationic monomer or polymer.

16. The method of claim 13 wherein said indicator reagent binds to substantially all Lp(a) via kringle 5 of apo(a), to plasminogen at less than 1% of Lp(a) binding and to LDL, VLDL, IDL and HDL at less than 2% of Lp(a) binding.

17. A method for determining the amount of Lp(a) in a sample comprising the steps of:
   (a) contacting said sample with an indicator reagent wherein said indicator reagent is a monoclonal antibody or fragment thereof that specifically binds to kringle 5 of apo(a) and with a solid support coated with Lp(a) for a time and under conditions to permit binding of said indicator reagent with said Lp(a) in said test sample and with said bound Lp(a); and
   (b) determining said amount of Lp(a) in said test sample by detecting the reduction in binding of said indicator reagent to said solid support as compared to the signal generated from a negative sample to indicate the presence of Lp(a) in said test sample.

18. The method of claim 17 wherein said monoclonal antibody binds to substantially all Lp(a) via kringle 5 of apo(a), to plasminogen at less than 1% of Lp(a) binding and to LDL, VLDL, IDL and HDL at less than 2% of Lp(a) binding.

19. The method of claim 17 wherein said monoclonal antibody is selected from the group consisting of Mab Nos. 1-532-266, 1-390-191, 1-458-165, 1-892-230, 1-292-189, 1-431-378, 1-746-183, and 1-546-264.

20. The method of claim 19 wherein at each occurrence therein, said labeled Lp(a) is replaced by labeled kringle 5 of apo(a).

21. The method of claim 17 wherein at each occurrence therein, said indicator reagent is replaced by labeled Lp(a) and said bound-Lp(a) is replaced by bound monoclonal antibody or a fragment thereof that specifically binds to kringle 5 of apo(a).

22. The method of claim 21 wherein said indicator reagent binds to substantially all Lp(a) via kringle 5 of apo(a), to plasminogen at less than 1% of Lp(a) binding and to LDL, VLDL, IDL and HDL at less than 2% of Lp(a) binding.

23. The method of claim 21 wherein said monoclonal antibody is selected from the group consisting of Mab Nos. 1-532-266, 1-390-191, 1-458-165, 1-892-230, 1-292-189, 1-431-378, 1-746-183, and 1-546-264.

24. A method for determining the amount of cholesterol associated with Lp(a) in a sample comprising:
 (a) contacting a sample and a monoclonal antibody or fragment thereof that binds to substantially all Lp(a) via kringle 5 of apo(a), to plasminogen at less than 1% of Lp(a) binding and to LDL, VLDL, IDL and HDL at less than 2% of Lp(a) binding, wherein said antibody is coupled to a solid support;
 (b) separating said solid support from said sample; and
 (c) determining said amount of cholesterol bound to said solid support.

25. A test kit for the detection and quantification of lp(a) in a plasma sample, comprising a reagent which binds to substantially all Lp(a) via kringle 5 of apo(a), to plasminogen at less than 1% of Lp(a) binding and to LDL, VLDL, IDL and HDL at less than 2% of Lp(a) binding.

26. The test kit of claim 25 wherein said reagent is labeled.

* * * * *

UNITED STATES PATENT AND TRADEMARK OFFICE
CERTIFICATE OF CORRECTION

PATENT NO.     : 6,210,906 B1                                        Page 1 of 1
DATED          : April 3, 2001
INVENTOR(S)    : Samar K. Kundu et al.

It is certified that error appears in the above-identified patent and that said Letters Patent is hereby corrected as shown below:

<u>Column 38,</u>
Lines 26-30, replace "(C)    (D)" with -- (B)    (C) --.

Signed and Sealed this

Twenty-sixth Day of November, 2002

Attest:

Attesting Officer

JAMES E. ROGAN
*Director of the United States Patent and Trademark Office*